United States Patent
Nagano et al.

(10) Patent No.: US 9,688,857 B2
(45) Date of Patent: Jun. 27, 2017

(54) FLUORESCENT PROBE

(71) Applicant: THE UNIVERSITY OF TOKYO, Tokyo (JP)

(72) Inventors: Tetsuo Nagano, Tokyo (JP); Kenjiro Hanaoka, Tokyo (JP); Yuichiro Koide, Tokyo (JP); Takahiro Egawa, Tokyo (JP); Kazuhisa Hirabayashi, Tokyo (JP)

(73) Assignee: THE UNIVERSITY OF TOKYO, Tokyo (JP)

( * ) Notice: Subject to any disclaimer, the term of this patent is extended or adjusted under 35 U.S.C. 154(b) by 0 days.

(21) Appl. No.: 15/292,858

(22) Filed: Oct. 13, 2016

(65) Prior Publication Data

US 2017/0096561 A1 Apr. 6, 2017

Related U.S. Application Data

(60) Continuation of application No. 14/854,779, filed on Sep. 15, 2015, which is a division of application No. 13/980,215, filed as application No. PCT/JP2012/051122 on Jan. 19, 2012, now Pat. No. 9,187,499.

(30) Foreign Application Priority Data

Jan. 20, 2011 (JP) ................................. 2011-009577
Feb. 18, 2011 (JP) ................................. 2011-033395

(51) Int. Cl.
  *C07F 7/30* (2006.01)
  *C09B 11/24* (2006.01)
  *C09B 69/00* (2006.01)
  *G01N 21/64* (2006.01)
  *G01N 33/84* (2006.01)

(52) U.S. Cl.
  CPC ............ *C09B 11/24* (2013.01); *C09B 69/008* (2013.01); *G01N 21/6428* (2013.01); *G01N 33/84* (2013.01); *G01N 2021/6439* (2013.01)

(58) Field of Classification Search
  CPC ......... C07F 7/0807; C07F 7/2212; C07F 7/30
  See application file for complete search history.

(56) References Cited

U.S. PATENT DOCUMENTS

| | | | |
|---|---|---|---|
| 2014/0057312 A1 | 2/2014 | Nagano et al. | |
| 2014/0342384 A1 | 11/2014 | Nagano et al. | |
| 2015/0185209 A1* | 7/2015 | Dyer | G01N 21/6428 530/300 |

FOREIGN PATENT DOCUMENTS

| | | |
|---|---|---|
| CN | 1810812 | 8/2006 |
| JP | 5526124 | 4/2014 |
| WO | 2010/126077 | 11/2010 |
| WO | 2011/055912 | 5/2011 |
| WO | 2012/083064 | 6/2012 |

OTHER PUBLICATIONS

Egawa et al, Chem.Commun., 2011,47,4162-4164.
Yuichiro Koide et al., "Fourth Convention of The Japanese Society for Molecular Imaging, subject No. P8-9", May 14, 2009.
Best, Q et al., "Pacifichem 2010, subject No. 2335" Dec. 19, 2010.
U.S. Appl. No. 13/985,185, filed Aug. 13, 2013, Tetsuo Nagano et al.
U.S. Appl. No. 13/985,119, filed Aug. 13, 2013, Tetsuo Nagano et al.
Search report from International Application No. PCT/JP2012/051122, mail date is Apr. 3, 2012.
International Preliminary Report on Patentability PCT/JP2012/051122 , mail date is Aug. 1, 2013.
Japanese Office Action in respect to Japanese Application No. 2012-553771, dated Jul. 31, 2015.

* cited by examiner

*Primary Examiner* — Sudhakar Katakam
(74) *Attorney, Agent, or Firm* — Greenblum & Bernstein, P.L.C.

(57) ABSTRACT

A compound represented by the formula (I) ($R^1$ represents hydrogen atom or a monovalent substituent; $R^2$ and $R^3$ represent hydrogen atom, an alkyl group, or a halogen atom; $R^4$ and $R^5$ represent an alkyl group or an aryl group; $R^6$ and $R^7$ represent hydrogen atom, an alkyl group, or a halogen atom; $R^8$ represent hydroxy group or a dialkoxyboranetriyl group; and X represents silicon atom, germanium atom, or tin atom), which is a novel fluorophore usable as a mother nucleus of an off/on type fluorescent probe not utilizing the intramolecular photoinduced electron transfer.

11 Claims, 8 Drawing Sheets

FLUORESCENT PROBE

CROSS-REFERENCE TO RELATED APPLICATIONS

The present application is a continuation application of U.S. application Ser. No. 14/854,779, filed Sep. 15, 2015, which is a divisional application of U.S. application Ser. No. 13/980,215, which is a National Stage of International Patent Application No. PCT/JP2012/051122, filed Jan. 19, 2012, which claims priority of JP 2011-009577, filed Jan. 20, 2011 and JP 2011-033395, filed Feb. 18, 2011. The entire disclosures of U.S. application Ser. Nos. 14/854,779 and 13/980,215, and International Application PCT/JP2012/051122 are expressly incorporated by reference herein.

TECHNICAL FIELD

The present invention relates to a fluorescent probe having a novel fluorophore.

BACKGROUND ART

Fluorescein is a molecule reported in 1871, and has been widely used as a pH indicator or a labeling dye because of the high water solubility and high fluorescence quantum yield thereof. Since a calcium probe containing fluorescein as a mother nucleus was developed, there have been provided a large number of highly sensitive fluorescent off/on type probes utilizing intramolecular photoinduced electron transfer (PET), decyclization or cyclization of spiro ring, and the like. However, plural dyes containing fluorescein as a parent compound cannot be simultaneously used in molecular imaging, since fluorescence wavelengths thereof overlap with each other. Moreover, the probes utilizing the intramolecular photoinduced electron transfer suffer from a problem that such probes require precise design of the oxidation potential of the benzene ring, and therefore modification of the chemical structure is strictly limited.

Further, almost no reports were made as for structural modification of fluorescein at the oxygen atom of the 10-position of the xanthene ring, and optical characteristics of such compounds, wherein the oxygen atom at the 10-position of the xanthene ring is replaced with another type of atom, are not known so far. Although a compound corresponding to the basic structure of rhodamine, pyronin Y (PY), of which oxygen atom is replaced with silicon atom (TMDHS) and application of this compound as a fluorescent probe have already been reported (Best, Q et al., Pacifichem 2010, subject number 2335, Dec. 19, 2010; Yuichiro KOIDE et al., Fourth Convention of The Japanese Society for Molecular Imaging, subject number P8-9, May 14, 2009), this fluorescent probe having TMDHS as the basic structure is basically a probe utilizing the intramolecular photoinduced electron transfer or decyclization or cyclization of spiro ring. In addition, any compound corresponding to fluorescein, of which oxygen atom at the 10-position of the xanthene ring is replaced with silicon atom, has not been reported so far, and fluorescent characteristics of such a compound are also not known.

PRIOR ART REFERENCES

Non-Patent Documents

Non-patent document 1: Best, Q et al., Pacifichem 2010, subject number 2335, Dec. 19, 2010

Non-patent document 2: Yuichiro KOIDE et al., Fourth Convention of The Japanese Society for Molecular Imaging, subject number P8-9, May 14, 2009

SUMMARY OF THE INVENTION

Object to be Achieved by the Invention

An object of the present invention is to provide a fluorescent probe having a novel fluorophore.

More specifically, the object of the present invention is to provide a compound which can be a novel fluorophore usable as a parent compound of a fluorescent off/on type probe not utilizing the intramolecular photoinduced electron transfer by chemically modifying the fluorescein structure, and provide a fluorescent probe utilizing such a compound.

Means for Achieving the Object

The inventors of the present invention conducted various researches to achieve the aforementioned object. As a result, they found that, as for a compound having the fluorescein structure in which the oxygen atom at the 10-position of the xanthene ring was replaced with silicon atom, the maximal absorption wavelengths of the non-dissociated form (neutral form) and dissociated form (anion form) of such a compound significantly deviated, and the difference of the wavelengths was about twice or more larger than that is observed in the non-dissociated form (neutral form) and dissociated form (anion form) of a fluorescein derivative (the oxygen atom at the 10-position of the xanthene ring is conserved). They also found that, by utilizing this characteristic, a fluorescent probe, capable of highly sensitive measurement of pH, various enzymes, and the like, was successfully provided without utilizing the intramolecular photoinduced electron transfer. The present invention was accomplished on the basis of the aforementioned findings.

The present invention thus provides a compound represented by the following general formula (I):

[Formula 1]

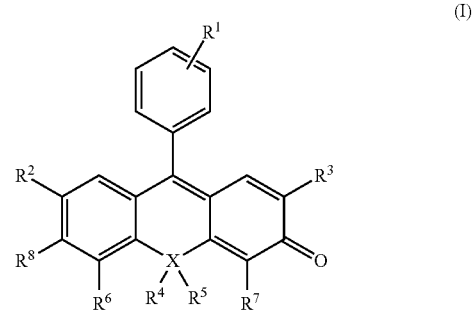

wherein, in the formula, $R^1$ represents hydrogen atom, or the same or different 1 to 5 monovalent substituents existing on the benzene ring; $R^2$ and $R^3$ independently represent hydrogen atom, an alkyl group having 1 to 6 carbon atoms, or a halogen atom; $R^4$ and $R^5$ independently represent an alkyl group having 1 to 6 carbon atoms, or an aryl group having 1 to 6 carbon atoms; $R^6$ and $R^7$ independently represent hydrogen atom, an alkyl group having 1 to 6 carbon atoms, or a halogen atom; $R^8$ represents hydroxy group, or a dialkoxyboranetriyl group; and X represents silicon atom, germanium atom, or tin atom, or a salt thereof.

According to a preferred embodiment of the aforementioned invention, there is provided the aforementioned compound or a salt thereof wherein $R^1$ represents hydrogen atom, or 1 to 3 monovalent substituents existing on the benzene ring (the substituents are selected from the group consisting of an alkyl group having 1 to 6 carbon atoms, an alkenyl group having 1 to 6 carbon atoms, an alkynyl group having 1 to 6 carbon atoms, an alkoxy group having 1 to 6 carbon atoms, hydroxy group, carboxy group, sulfonyl group, an alkoxycarbonyl group, a halogen atom, and amino group), $R^2$ and $R^3$ independently represent hydrogen atom, an alkyl group having 1 to 6 carbon atoms, or a halogen atom, $R^4$ and $R^5$ independently represent an alkyl group having 1 to 6 carbon atoms, $R^6$ and $R^7$ independently represent hydrogen atom, or an alkyl group having 1 to 6 carbon atoms, $R^8$ represents hydroxy group, or (pinacolato) boranetriyl group; and X represents a silicon atom. According to a further preferred embodiment, there is provided the aforementioned compound or a salt thereof, wherein $R^1$ represents hydrogen atom, or 1 to 3 monovalent substituents existing on the benzene ring (the substituents are selected from the group consisting of an alkyl group having 1 to 6 carbon atoms, an alkoxy group having 1 to 6 carbon atoms, hydroxy group, carboxy group, a halogen atom, and amino group), $R^2$ and $R^3$ independently represent hydrogen atom, or a halogen atom, $R^4$ and $R^5$ independently represent an alkyl group having 1 to 8 carbon atoms, $R^6$ and $R^7$ are both hydrogen atoms, both chlorine atoms, or both fluorine atoms, $R^8$ represents hydroxy group; and X represents silicon atom.

From other aspects of the present invention, there are provided the aforementioned compound represented by the general formula (I) or a salt thereof, which is for use in manufacture of a fluorescent probe, and use of the aforementioned compound represented by the general formula (I) or a salt thereof for manufacture of a fluorescent probe.

The present invention also provides a compound represented by the following general formula (II):

[Formula 2]

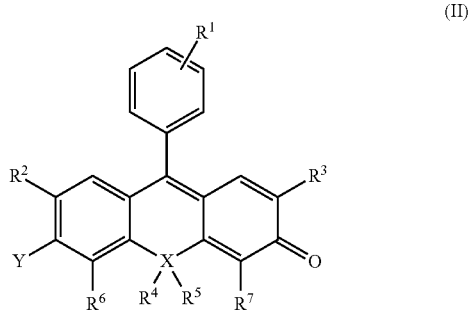

(II)

wherein, in the formula, $R^1$, $R^2$, $R^3$, $R^4$, $R^5$, $R^6$, $R^7$, and X have the same meanings as those defined above, and Y represents $OR^{11}$ ($R^{11}$ represents hydrogen atom, or a monovalent group that is cleaved by contact with an object substance for measurement) or a dialkoxyboranetriyl group, or a salt thereof.

According to preferred embodiments, there are provided the aforementioned compound or a salt thereof, wherein $R^1$ represents hydrogen atom, or 1 to 3 monovalent substituents existing on the benzene ring (the substituents are selected from the group consisting of an alkyl group having 1 to 6 carbon atoms, an alkoxy group having 1 to 6 carbon atoms, hydroxy group, carboxy group, sulfonyl group, an alkoxycarbonyl group, a halogen atom, and amino group), $R^2$ and $R^3$ independently represent hydrogen atom, an alkyl group having 1 to 6 carbon atoms, or a halogen atom, $R^4$ and $R^5$ independently represent an alkyl group having 1 to 6 carbon atoms, $R^6$ and $R^7$ independently represent hydrogen atom, or an alkyl group having 1 to 6 carbon atoms, or they are both chlorine atoms or both fluorine atoms, X is silicon atom, and Y is $OR^{11}$ ($R^{11}$ is a monovalent group that is cleaved by an enzyme), or (pinacolato)boranetriyl group; the aforementioned compound or a salt thereof wherein $R^{11}$ is hydrogen atoms, or a monovalent group that is cleaved by a reductase, an oxidase, or a hydrolase; and the aforementioned compound or a salt thereof wherein $R^{11}$ is hydrogen atom, or a monovalent group that is cleaved by an enzyme selected from the group consisting of β-lactamase, cytochrome P450 oxidase, β-galactosidase, β-glucosidase, β-glucuronidase, β-hexosaminidase, lactase, alkaline phosphatase, matrix metalloproteinase, and glutamyl transferase.

As another aspect, the present invention provides a pH fluorescent probe containing a compound represented by the aforementioned general formula (II) (in the formula, $R^1$, $R^2$, $R^3$, $R^4$, $R^5$, and X have the same meanings as those defined above, and Y represents hydroxy group) or a salt thereof.

The present invention also provides a method for measuring pH, which comprises the step of measuring pH by using a compound represented by the aforementioned general formula (II) (in the formula, $R^1$, $R^2$, $R^3$, $R^4$, $R^5$, and X have the same meanings as those defined above, and Y represents hydroxy group) or a salt thereof as a fluorescent probe, and a method for measuring pH, which comprises the step of contacting a cell, tissue, or body fluid with a compound represented by the aforementioned general formula (II) (in the formula, $R^1$, $R^2$, $R^3$, $R^4$, $R^5$, and X have the same meanings as those defined above, and Y represents hydroxy group) or a salt thereof and then measuring fluorescence.

From still another aspect, the present invention provides a fluorescent probe containing a compound represented by the aforementioned general formula (II) (in the formula, $R^1$, $R^2$, $R^3$, $R^4$, $R^5$, and X have the same meanings as those defined above, and Y represents $OR^{11}$ ($R^{11}$ represents a monovalent group that is cleaved by contact with an object substance for measurement), or a dialkoxyboranetriyl group), or a salt thereof.

The present invention also provides a method for measuring an object substance for measurement, which comprises the step of contacting the object substance for measurement with a compound represented by the aforementioned general formula (II) (in the formula, $R^1$, $R^2$, $R^3$, $R^4$, $R^5$, and X have the same meanings as those defined above, and Y represents $OR^{11}$ ($R^{11}$ represents a monovalent group that is cleaved by contact with an object substance for measurement), or a dialkoxyboranetriyl group, or a salt thereof and then measuring fluorescence.

From still another aspect, the present invention provides a method for preparing a compound represented by the aforementioned general formula (I) or a salt thereof, which comprises:

(a) the step of preparing a compound represented by the following general formula (III):

[Formula 3]

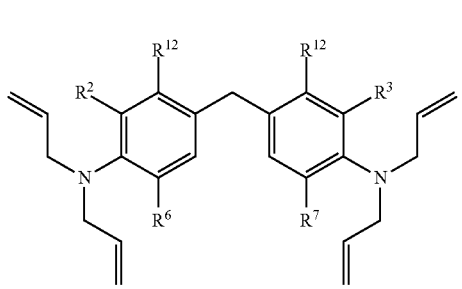

(III)

(in the formula, $R^{12}$ represents a halogen atom, and $R^2$, $R^3$, $R^6$, and $R^7$ have the same meanings as those defined above) from a 3-halogenated N,N-diallylaniline, which is prepared from a 3-halogenated aniline and an allyl halide, and formaldehyde, (b) the step of reacting the compound represented by the aforementioned general formula (III) with $X(Halo)_2(R^4)(R^5)$ (Halo represents chlorine atom or bromine atom, and X, $R^4$, and $R^5$ have the same meanings as those defined above), and then subjecting the resultant to an oxidation reaction to prepare an N,N,N',N'-tetrallyl-diamino-X-xanthone mentioned below,

[Formula 4]

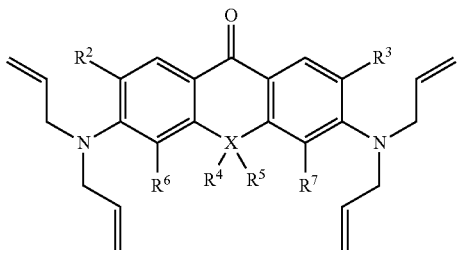

(c) the step of subjecting the N,N,N',N'-tetrallyl-diamino-X-xanthone to deallylation to prepare a diamino-X-xanthone mentioned below,

[Formula 5]

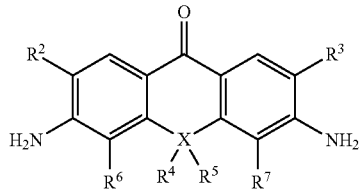

(d) the step of converting the amino groups of the diamino-X-xanthone into hydroxy groups to prepare a dihydroxy-X-xanthone mentioned below,

[Formula 6]

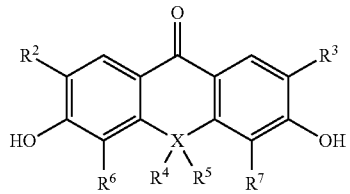

(e) the step of protecting the hydroxy groups of the dihydroxy-X-xanthone with protective groups to prepare a compound represented by the following general formula (IV):

[Formula 7]

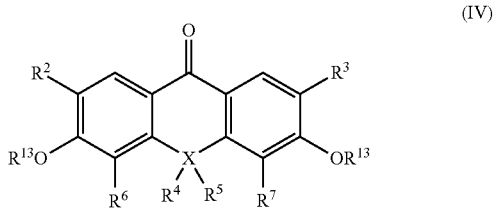

(IV)

(in the formula, $R^{13}$ represents a protective group of phenolic hydroxy group, or a dialkoxyboranetriyl group), and (f) the step of preparing a compound represented by the aforementioned general formula (I) or a salt thereof from the compound represented by the aforementioned general formula (IV) and a halogenated benzene derivative.

$R^2$, $R^3$, $R^6$, and $R^7$ are preferably hydrogen atoms, Halo is preferably chlorine atom, and $R^4$ and $R^5$ are preferably methyl groups.

The present invention also provides the aforementioned method for preparing a compound represented by the general formula (I) or a salt thereof, which comprises the aforementioned step (f); the aforementioned method for preparing a compound represented by the general formula (I) or a salt thereof, which comprises the aforementioned steps (e) and (f); the aforementioned method for preparing a compound represented by the general formula (I) or a salt thereof, which comprises the aforementioned steps (d), (e), and (f); the aforementioned method for preparing a compound represented by the general formula (I) or a salt thereof, which comprises the aforementioned steps (c), (d), (e), and (f); and the aforementioned method for preparing a compound represented by the general formula (I) or a salt thereof, which comprises the aforementioned steps (b), (c), (d), (e), and (f).

The present invention also provides the aforementioned method for preparing a compound represented by the aforementioned general formula (I) or a salt thereof wherein a compound wherein $R^6$ and $R^7$ are both hydrogen atoms is used as a starting material in the step (a), the resultant of the step (d) is reacted with a chlorinating agent or a fluorinating agent to prepare a compound wherein $R^6$ and $R^7$ are both chlorine atoms, or $R^6$ and $R^7$ are both fluorine atoms, and this compound is used as a starting compound to perform the steps (e) and (f) and thereby prepare a compound represented by the general formula (I) wherein $R^6$ and $R^7$ are both chlorine atoms or both fluorine atoms. The present invention also provides a method for preparing the dihydroxy-X-xanthone compound wherein $R^6$ and $R^7$ are both chlorine atoms, or $R^6$ and $R^7$ are both fluorine atoms, which comprises reacting the dihydroxy-X-xanthone compound mentioned in the aforementioned step (d) wherein $R^6$ and $R^7$ are both hydrogen atoms with a chlorinating agent or a fluorinating agent.

Further, by reacting 2,7-substituted or 2,7-unsubstituted 3,6-dihydroxyxanthone with a chlorinating agent or a fluorinating agent, 2,7-substituted or 2,7-unsubstituted 4,5-dichloro-3,6-dihydroxyxanthone, or 2,7-substituted or 2,7-unsubstituted 4,5-difluoro-3,6-dihydroxyxanthone can be prepared. Furthermore, by protecting the hydroxy groups at the 3- and 6-positions of 2,7-substituted or 2,7-unsubstituted 4,5-dichloro-3,6-dihydroxyxanthone, or 2,7-substituted or 2,7-unsubstituted 4,5-difluoro-3,6-dihydroxyxanthone with protective groups, then reacting the protected compound with a halogenated benzene derivative, and removing the protective groups of the hydroxy groups, 2,7-substituted or 2,7-unsubstituted 4,5-dichloro-3,6-dihydroxyxanthen-9-yl, or 2,7-substituted or 2,7-unsubstituted 4,5-difluoro-3,6-dihydroxyxanthen-9-yl to which a substituted phenyl group is bound at the 9-position can be prepared.

As a particularly preferred embodiment of the aforementioned method, there is provided a method for preparing a compound represented by the aforementioned general formula (I) (in the formula, $R^2$, $R^3$, $R^6$, and $R^7$ are hydrogen atoms, $R^4$ and $R^5$ are methyl groups, and $R^8$ represents hydroxy group) or a salt thereof, which comprises:

(a) the step of preparing a compound represented by the following general formula (IIIa):

[Formula 8]

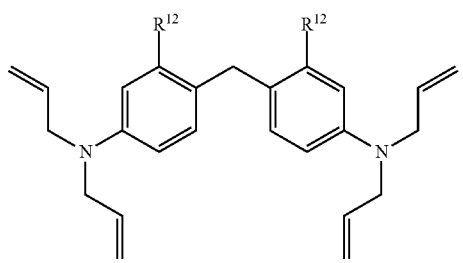

(IIIa)

(in the formula, $R^{12}$ represents a halogen atom) from a 3-halogenated N,N-diallylaniline, which is prepared from a 3-halogenated aniline and an allyl halide, and formaldehyde, (b) the step of reacting the compound represented by the aforementioned general formula (IIIa) with dichlorodimethylsilane, and subjecting the resultant to an oxidation reaction to prepare N,N,N',N'-tetrallyl-diamino-Si-xanthone mentioned below,

[Formula 9]

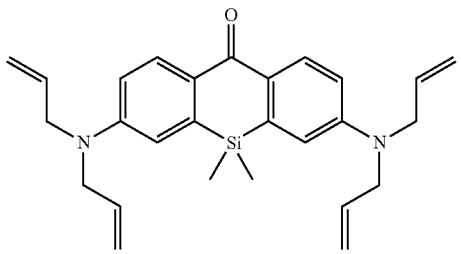

(c) the step of preparing diamino-Si-xanthone mentioned below by subjecting the N,N,N',N'-tetrallyl-diamino-Si-xanthone to deallylation,

[Formula 10]

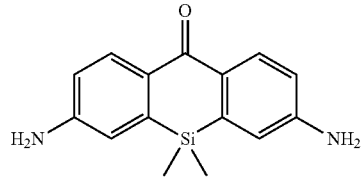

(d) the step of converting the amino groups of the diamino-Si-xanthone into hydroxy groups to prepare dihydroxy-Si-xanthone mentioned below,

[Formula 11]

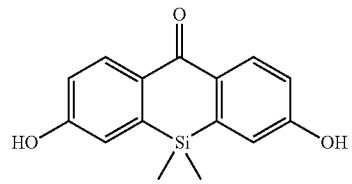

(e) the step of protecting the hydroxy groups of the dihydroxy-Si-xanthone with protective groups to prepare a compound represented by the following general formula (IVa):

[Formula 12]

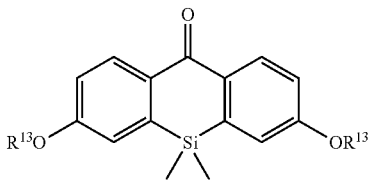

(IVa)

(in the formula, $R^{13}$ represents a protective group of phenolic hydroxy group), and (f) the step of preparing a compound represented by the aforementioned general formula (I) ($R^2$, $R^3$, $R^6$ and $R^7$ are hydrogen atoms, $R^4$ and $R^5$ are methyl groups, and $R^8$ represents hydroxy group) or a salt thereof from the compound represented by the aforementioned general formula (IVa) and a halogenated benzene derivative.

The present invention also provides the aforementioned method for preparing a compound represented by the general formula (I) (in the formula, $R^2$, $R^3$, $R^6$ and $R^7$ are hydrogen atoms, $R^4$ and $R^5$ are methyl groups, and $R^8$ represents hydroxy group) or a salt thereof, which comprises the aforementioned step (f); the aforementioned method for preparing a compound represented by the general formula (I) (in the formula, $R^2$, $R^3$, $R^6$ and $R^7$ are hydrogen atoms, $R^4$ and $R^5$ are methyl groups, and $R^8$ represents hydroxy group) or a salt thereof, which comprises the aforementioned steps (e) and (f); the aforementioned method for preparing a compound represented by the general formula (I) (in the formula, $R^2$, $R^3$, $R^6$ and $R^7$ are hydrogen atoms, $R^4$ and $R^5$ are methyl groups, and $R^8$ represents hydroxy group) or a salt thereof, which comprises the aforementioned steps (d), (e), and (f); the aforementioned method for preparing a compound represented by the general formula (I) (in the formula, $R^2$, $R^3$, $R^6$ and $R^7$ are hydrogen atoms, $R^4$ and $R^5$ are methyl groups, and $R^8$ represents hydroxy group) or a salt thereof, which comprises the aforementioned steps (c), (d), (e), and (f); and the aforementioned method for preparing a compound represented by the general formula (I) (in the formula, $R^2$, $R^3$, $R^6$ and $R^7$ are hydrogen atoms, $R^4$ and $R^5$ are methyl groups, and $R^8$ represents hydroxy group) or a salt thereof, which comprises the aforementioned steps (b), (c), (d), (e), and (f).

Effect of the Invention

The compounds represented by the general formula (I) and salts thereof provided by the present invention show significantly deviated maximal absorption wavelengths between the non-dissociated form (neutral form) and dissociated form (anion form) of the compounds, of which difference is about twice or more larger than that of a fluorescein derivative. Therefore, when this property is utilized, they are useful as a parent compound for manufacture of a fluorescent probe that is capable of highly sensitive measurement of pH, reactive oxygen species, various enzymes and the like without depending on the intramolecular photoinduced electron transfer or control of cyclisation of spiro ring. The compounds represented by the aforementioned general formula (II) and salts thereof are also useful as a fluorescent probe that successfully achieves highly sensitive measurement of pH, reactive oxygen species, various enzymes and the like without depending on the intramolecular photoinduced electron transfer.

MODES FOR CARRYING OUT THE INVENTION

Figure 1:
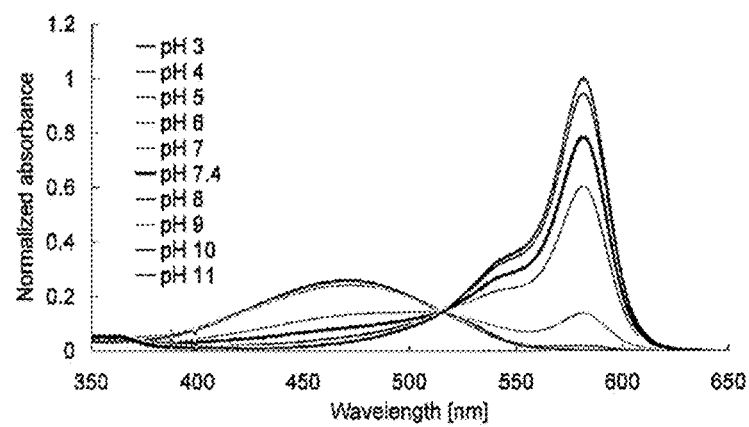
FIG. 1 shows results of measurement of absorption spectra and fluorescence spectra of 2-Me TokyoMagenta, which is a typical example of the compound of the present invention (in this specification, "TokyoMagenta" represents a compound of the general formula (I) wherein $R^1$ is hydrogen atom, $R^2$ and $R^3$ are hydrogen atoms, $R^4$ and $R^5$ are methyl groups, $R^6$ and $R^7$ are hydrogen atoms, $R^8$ is hydroxy group, and X is silicon atom, and this compound may be abbreviated as "TM"). The measurement was performed with changing pH. In this specification, Me means methyl group. The upper graph shows absorption spectra and the lower graph shows fluorescence spectra (excitation wavelength, 550 nm). The measurement was performed by using a 1 μM solution of 2-Me TokyoMagenta dissolved in a 0.1 M phosphate buffer containing 1% dimethyl sulfoxide (DMSO).
Figure 1:
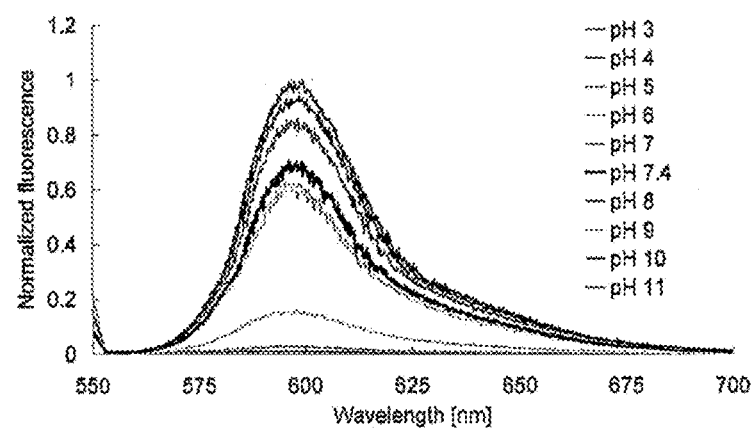

In the specification, "an alkyl group" or an alkyl moiety of a substituent containing an alkyl moiety (for example, an alkoxy group, and the like) means a linear, branched, or cyclic alkyl group, or an alkyl group consisting of a combination thereof, having, for example, 1 to 6 carbon atoms, preferably 1 to 4 carbon atoms, more preferably 1 to 3 carbon atoms, unless specifically indicated. More specifically examples of the alkyl group include, for example, methyl group, ethyl group, n-propyl group, isopropyl group, cyclopropyl group, n-butyl group, sec-butyl group, isobutyl group, tert-butyl group, cyclopropylmethyl group, n-pentyl group, n-hexyl group, and the like. The "halogen atom" referred to in the specification may be any one of fluorine atom, chlorine atom, bromine atom, and iodine atom, preferably, fluorine atom, chlorine atom, or bromine atom.

In the compound represented by the general formula (I), $R^1$ represents hydrogen atom, or the same or different 1 to 5 monovalent substituents existing on the benzene ring. When $R^1$ represents the monovalent substituents existing on the benzene ring, it is preferred that the same or different about 1 to 3 substituents exist on the benzene ring. When $R^1$ represents one or two or more monovalent substituents, the substituents can substitute at arbitrary positions on the benzene ring, but it is preferred that, for example, one substituent exists at the ortho-position with respect to the binding position of the condensed ring containing X on the benzene ring. When two or more substituents exist on the benzene ring, it is preferred that one of the substituents exists at the ortho-position with respect to the binding position of the condensed ring containing X. It is preferred that $R^1$ represents hydrogen atom, or one substituent existing at the ortho-position with respect to the binding position of the condensed ring containing X. It is also preferred that, for example, $R^1$ represents two monovalent substituents.

Although type of the monovalent substituent as $R^1$ is not particularly limited, it is preferably selected from, for example, the group consisting of an alkyl group having 1 to 6 carbon atoms, an alkenyl group having 1 to 6 carbon atoms, an alkynyl group having 1 to 6 carbon atoms, an alkoxy group having 1 to 6 carbon atoms, hydroxy group, carboxy group, sulfonyl group, an alkoxycarbonyl group, a halogen atom, and amino group. These monovalent substituents may further have one or two or more arbitrary substituents. For example, the alkyl group as $R^1$ may have one or more of substituents selected from a halogen atom, carboxy group, sulfonyl group, hydroxy group, amino group, an alkoxy group, and the like, and the alkyl group as $R^1$ may be, for example, a halogenated alkyl group, a hydroxyalkyl group, a carboxyalkyl group, an aminoalkyl group, or the like. The amino group as $R^1$ may have one or two alkyl groups, and the amino group as $R^1$ may be, for example, a monoalkylamino group or a dialkylamino group. Further, when the alkoxy group as by $R^1$ has a substituent, examples thereof include, for example, a carboxy-substituted alkoxy group, an alkoxycarbonyl-substituted alkoxy group, and the like, more specifically, 4-carboxybutoxy group, 4-acetoxymethyloxycarbonylbutoxy group, and the like.

When $R^1$ represents two monovalent substituents, they are preferably selected from, for example, the group consisting of an alkyl group having 1 to 6 carbon atoms, an alkoxy group having 1 to 6 carbon atoms, and carboxy group, and they are more preferably selected from the group consisting of an alkyl group having 1 to 6 carbon atoms, and an alkoxy group having 1 to 6 carbon atoms. In this case, it is preferred that an alkyl group having 1 to 6 carbon atoms exists at the ortho-position with respect to the binding position of the condensed ring containing X, and an alkoxy group (for example, an unsubstituted alkoxy group, a monocarboxy group-substituted alkoxy group, a monoalkoxycarbonyl-substituted alkoxy group, 4-acetoxymethyloxycarbonylbutoxy group and the like) exists at another position on the benzene ring.

$R^2$ and $R^3$ independently represent hydrogen atom, an alkyl group having 1 to 6 carbon atoms, or a halogen atom. When $R^2$ or $R^3$ represents an alkyl group, the alkyl group may have one or two or more substituents selected from a halogen atom, carboxy group, sulfonyl group, hydroxy group, amino group, an alkoxy group, and the like, and the alkyl group as $R^2$ or $R^3$ may be, for example, a halogenated alkyl group, a hydroxyalkyl group, a carboxyalkyl group, or the like. It is preferred that $R^2$ and $R^3$ are independently hydrogen atom or a halogen atom, and it is more preferred that $R^2$ and $R^3$ are both hydrogen atoms, or $R^2$ and $R^3$ are both chlorine atoms or fluorine atoms.

$R^4$ and $R^5$ independently represent an alkyl group having 1 to 6 carbon atoms, or an aryl group having 1 to 6 carbon atoms. It is preferred that $R^4$ and $R^5$ are independently an alkyl group having 1 to 3 carbon atoms, and it is more preferred that $R^4$ and $R^5$ are both methyl groups. The alkyl group as $R^4$ or $R^5$ may have one or two or more substituents selected from a halogen atom, carboxy group, sulfonyl group, hydroxy group, amino group, an alkoxy group, and the like, and the alkyl group as $R^4$ or $R^5$ may be, for example, a halogenated alkyl group, a hydroxyalkyl group, a carboxyalkyl group, or the like. When $R^4$ or $R^5$ represents an aryl group, the aryl group may be a monocyclic aromatic group, or a condensed ring aromatic group, and the aryl ring may contain one or two or more ring-constituting heteroatoms (for example, nitrogen atom, sulfur atom, oxygen atom and the like). As the aryl group, phenyl group is preferred. The aryl ring may have one or two or more substituents on the ring. As the substituents, for example, one or two or more substituents selected from a halogen atom, carboxy group, sulfonyl group, hydroxy group, amino group, an alkoxy group, and the like may exist.

$R^6$ and $R^7$ independently represent hydrogen atom, an alkyl group having 1 to 6 carbon atoms, or a halogen atom, and these are the same as those explained for $R^2$ and $R^3$. It is preferred that $R^6$ and $R^7$ are both hydrogen atoms, both chlorine atoms, or both fluorine atoms.

X represents silicon atom, germanium atom, or tin atom. It is preferably silicon atom or germanium atom, and it is particularly preferably silicon atom.

$R^8$ represents hydroxy group, or a dialkoxyboranetriyl group. The carbon numbers of two alkoxy groups existing in the dialkoxyboranetriyl group are, for example, about 1 to 6, and these alkoxy groups may combine together to form, for example, a 5-membered ring or 6-membered ring. This 5-membered ring or 6-membered ring may have about 1 to 4 substituents, for example, an alkyl group having about 1 to 6 carbon atoms. The dialkoxy group can also be introduced by reacting a diol compound with boron atom, and examples of such a case include, for example, binding a diol compound such as ethylene glycol, propylene glycol, pinacol, neopentyl glycol, and catechol, with boron atom. Examples of the dialkxyboranetriyl group include, for example, dimethozyboranetriyl group, tetramethylethylenedioxy-boranetriyl group, ((pinacolato)boron), o-phenylenedioxyboranetriyl group, and the like, but it is not limited to these examples. Among them, (pinacolato)boron is preferred.

In the compound represented by the general formula (II), $R^1$, $R^2$, $R^3$, $R^4$, $R^5$, $R^6$, $R^7$, and X have the same meanings as those defined above. Y represents $OR^{11}$ ($R^{11}$ represents hydrogen atom, or a monovalent group that is cleaved by contact with an object substance for measurement), or a dialkoxyboranetriyl group. As $R^{11}$ in Y, besides hydrogen atom, a group having a property that it is cleaved by contact with an object substance for measurement can be used. The dialkoxyboranetriyl group as Y is also the same as that defined above.

Type of the object substance for measurement is not particularly limited, and it may be any of for example, an enzyme, a metal ion (for example, alkali metal ion such as sodium ion and lithium ion, alkaline earth metal ion such as calcium ion, magnesium ion, zinc ion, and the like), a nonmetallic ion (carbonate ion and the like), reactive oxygen species (for example, hydroxy radical, peroxynitrite, hypochlorous acid, hydrogen peroxide, and the like), and the like. The substance is preferably an enzyme.

Examples of the enzyme include, for example, reductase, oxidase, hydrolase, and the like. Examples of the enzyme include enzymes useful for diagnosis of infectious diseases and cancers, such as β-lactamase, cytochrome P450 oxidase, β-galactosidase, β-glucosidase, β-glucuronidase, β-hexoaminidase, lactase, alkaline phosphatase, matrix metalloproteinase, glutamyl transferase, and the like, but the enzyme is not limited to these examples. Among the enzymes, hydrolase is especially preferred. Typical examples of the hydrolase include, for example, β-galactosidase, β-lactamase, alkaline phosphatase, matrix metalloproteinase, glutamyl transferase, and the like, but the hydrolase is not necessarily limited to those mentioned above.

When the object substance for measurement is a hydrolase, the compound of the general formula (II) can be designed so that the compound is hydrolyzed by the enzyme to give a compound wherein $R^{11}$ is hydrogen atom by choosing a compound that can serve as a specific substrate of the enzyme and functional groups. For example, when the object substance for measurement is a saccharide hydrolase, a residue of a saccharide compound that can be a substrate of the enzyme can be used as $R^{11}$. Functional groups of the saccharide compound, such as hydroxy group and amino group, may be protected with appropriate protective groups, if needed. Any of such compounds having a protective group also falls within the scope of the present invention.

When $R^{11}$ is p-aminophenyl group or p-hydroxyphenyl group, the compound is decomposed by contact with a reactive oxygen species to give a compound wherein $R^{11}$ is hydrogen atom, and therefore a reactive oxygen species can be used as the object substance for measurement. Fluorescent probes for reactive oxygen species having p-aminophenyl group or p-hydroxyphenyl group are described in, for example, International Patent Publications WO2001/064664, WO2004/040296, U.S. Pat. No. 7,378,282, and the like, and therefore the fluorescent probe of the present invention can be used in the same manner as those for the fluorescent probes disclosed in these references.

Further, when Y is a dialkoxyboranetriyl group, the compound is decomposed by contact with hydrogen peroxide to give a compound where Y is hydroxy group, and therefore hydrogen peroxide can be used as the object substance for measurement in such a case. Fluorescent probes for hydrogen peroxide having a dialkoxyboranetriyl group are described in, for example, Nature Chemical Biology, 3, pp. 263-267, 2007; J. Am. Chem. Soc., 132, pp. 4455-4465, 2010; J. Am. Chem. Soc., 132, pp. 5906-5915, 2010, and the like, and therefore the fluorescent probe of the present invention can be used in the same manner as those for the fluorescent probes disclosed in these references.

Further, the compound of the general formula (II) where $R^{11}$ in $OR^{11}$ as Y represents hydrogen atom reacts with glucuronic acid transferase and changes into a O-glycoside compound, and therefore the compound can measure the glucuronic acid transferase activity. That is, the compound wherein $R^{11}$ is hydrogen atom is in a dissociated form (anion form) in the physiological pH region around neutral before the reaction with glucuronic acid transferase, but the compound that becomes an O-glycoside compound after the reaction with glucuronic acid transferase is in a non-dissociated form (neutral form) showing an absorption wavelength significantly shifted to the shorter wavelength side and different fluorescence profile. For example, if fluorescence intensity of the compound wherein $R^{11}$ is hydrogen atom is measured with an excitation wavelength of 582 nm before and after the reaction with glucuronic acid transferase, strong fluorescence is observed around 600 nm before the reaction with glucuronic acid transferase, but after the reaction, the compound that became an O-glycoside compound does not have absorption at 582 nm, and therefore fluorescence is scarcely observed. Further, for example, if fluorescence intensity of the compound where $R^{11}$ is hydrogen atom is measured with an excitation wavelength of 471 nm before and after the reaction with glucuronic acid transferase, fluorescence intensity around 560 nm increases with advance of the reaction with glucuronic acid transferase. Specific examples of fluorescent probe for measurement of the glucuronic acid transferase activity utilizing a fluorescein derivative are disclosed in International Patent Publication WO2008/105376, and accordingly, the compounds of the present invention represented by the general formula (II) wherein $R^{11}$ is hydrogen atom can be used in the same manner as that of the probe disclosed in the above reference.

The compounds represented by the aforementioned general formulas (I), (II), (III), and (IV) may exist as a salt. Examples of the salt include base addition salts, acid addition salts, amino acid salts, and the like. Examples of the base addition salts include, for example, metal salts such as sodium salt, potassium salt, calcium salt and magnesium salt, ammonium salts, and organic amine salts such as triethylamine salt, piperidine salt, and morpholine salt, and examples of the acid addition salts include, for example, mineral acid salts such as hydrochloride, sulfate, and nitrate, and organic acid salts such as methanesulfonate, para-toluenesulfonate, citrate, and oxalate. As the amino acid salt, glycine salt, and the like can be exemplified. However, the salts of the compounds of the present invention are not limited to these examples.

The compounds of the present invention represented by the general formula (I) or (II) may have one or two or more asymmetric carbons depending to types of substituents, and they may exist as a stereoisomer such as enantiomer or diastereoisomer. Stereoisomers in pure form, arbitrary mixtures of stereoisomers, racemates, and the like all fall within the scope of the present invention. Further, the compounds of the present invention represented by the general formula (I) or (II) and salts thereof may exist as a hydrate or a solvate, and all of these substances are encompassed by the scope of the present invention. Type of the solvent that forms the solvate is not particularly limited, and examples include, for example, such solvents as ethanol, acetone, and isopropanol.

The compounds of the present invention represented by the general formula (I) have a characteristic feature that a non-dissociated form (neutral form) compound and a dissociated form (anion form) compound thereof show significantly deviated maximal absorption wavelengths, of which difference is about twice or more larger than the difference of the wavelengths of non-dissociated form (neutral form) and dissociated form (anion form) of a fluorescein derivative (the oxygen atom at the 10-position of the xanthene ring is conserved). Therefore, the compounds represented by the general formula (II) wherein $R^{11}$ is hydrogen atom (corresponding to the compounds represented by the general formula (I)) have a characteristic feature that the maximal absorption wavelength thereof significantly changes with pH change, and can be used as a fluorescent probe for pH detection. Further, the compounds represented by the general formula (II) wherein $R^{11}$ in Y is not hydrogen atom exists substantially as a non-dissociated form compound, but when $R^{11}$ is cleaved by contact with an object substance for measurement, a dissociated form compound is generated. Therefore, they have a characteristic feature that maximal absorption wavelength observed after contact with the object substance for measurement significantly changes from that observed before the contact, and can be used as a fluorescent probe for measuring the object substance for measurement at high sensitivity. In addition, when Y is a dialkoxyboranetriyl group, the compounds are decomposed by contact with hydrogen peroxide to generate a compound wherein Y is hydroxy group (dissociated form), and therefore the compounds wherein Y is a dialkoxyboranetriyl group have a characteristic feature that the maximal absorption wavelength observed after the contact with hydrogen peroxide as the object substance for measurement significantly changes from that observed before the contact, and can be similarly used as a fluorescent probe for measuring hydrogen peroxide at high sensitivity. As described above, the compounds represented by the general formula (I) are useful for manufacture of a probe that utilizes the difference of the maximal absorption wavelengths between a non-dissociated form compound and a dissociated form compound, and they do not utilize the intramolecular photoinduced electron transfer. Therefore, they have a characteristic feature that it is not necessary to strictly adjust the electron density (oxidation potential) of the benzene ring, and even if various substituents exist on the benzene ring, it can function as a probe.

For example, the compounds of the general formula (II) having 4-acetoxymethyloxycarbonylbutoxy group or the like as $R^1$ are efficiently incorporated into cells because of high lipophilicity thereof and when they are incorporated into cells, they are converted into a compound of the general formula (II) having high water solubility by hydrolysis of the 4-acetoxymethyloxycarbonylbutoxy group by an esterase existing in the cells, and then stay in the cells for a long period of time. Therefore, they are extremely suitable for imaging of an object substance for measurement in the cells. These compounds also do not utilize the intramolecular photoinduced electron transfer, and 4-acetoxymethyloxycarbonylbutoxy group can be introduced at an arbitrary position on the benzene ring, and therefore it provides high degree of freedom for design of fluorescent probes. The fluorescent probe is preferably designed so that the difference of fluorescence maximal absorption wavelengths observed before and after the cleavage of $R^{11}$ by an object substance for measurement is made as large as possible. Further, the fluorescent probe is more preferably designed so that, in addition to the aforementioned characteristic features, it is substantially non-fluorescent before the cleavage of $R^{11}$, and becomes strongly fluorescent after the cleavage of $R^{11}$.

The term "measurement" used in this specification should be construed in its broadest sense including quantification, qualification, as well as measurement, examination, detection, and the like performed for the purposes of diagnosis and the like. The method for measuring an object substance for measurement utilizing the fluorescent probe of the present invention wherein $R^{11}$ in Y is not hydrogen atom generally comprises (a) the step of contacting a compound represented by the aforementioned formula (II) with an object substance for measurement to cleave $R^{11}$, and (b) the step of measuring fluorescence of the compound generated in the aforementioned step (a) (corresponding to a dissociated form compound formed by the cleavage of $R^{11}$). The method for measuring an object substance for measurement utilizing the fluorescent probe of the present invention wherein Y is a dialkoxyboranetriyl group generally comprises (a) the step of contacting the compound represented by the aforementioned formula (II) with hydrogen peroxide, which is generally the object substance for measurement, to generate the compound where Y is hydroxy group, and (b) the step of measuring fluorescence of the compound generated in the aforementioned step (a). For example, the fluorescent probe of the present invention or a salt thereof can be dissolved in an aqueous medium such as physiological saline and buffer, a mixture of the aqueous medium and a water-miscible organic solvent such as ethanol, acetone, ethylene glycol, dimethyl sulfoxide, and dimethylformamide, or the like, this solution can be added to an appropriate buffer containing cells or tissues, and fluorescence spectrum can be measured before and after contact with the object substance for measurement.

Fluorescence of the compound of which $R^{11}$ has been cleaved by the object substance for measurement can be measured by a usual method, and a method of measuring a fluorescence spectrum in vitro, a method of measuring a fluorescence spectrum in vivo by using a bioimaging technique, and the like can be employed. For example, when quantification is performed, it is desirable to create a calibration curve beforehand in a conventional manner.

The fluorescent probe of the present invention may be mixed with additives usually used for preparation of reagents when required, and used as a composition. For example, as additives for using a reagent in a physiological environment, such additives as dissolving aids, pH modifiers, buffering agents, and isotonic agents can be used, and amounts of these can be appropriately selected by those skilled in the art. Such a composition is provided as a composition in an appropriate form such as powdery mixture, lyophilized product, granule, tablet, and solution.

The compounds prepared by the aforementioned preparation steps (a) to (e) of the method for preparing the compound of the present invention represented by the aforementioned the general formula (I) or a salt thereof comprising the steps (a) to (e) are novel compounds, and they are useful as synthetic intermediates for the preparation of the compounds of the present invention represented by the aforementioned general formula (I) and salts thereof. In the aforementioned preparation method, it is preferred that $R^2$ and $R^3$ are hydrogen atoms, it is preferred that $R^6$ and $R^7$ are both hydrogen atoms, both chlorine atoms, or both fluorine atoms, it is preferred that Halo is chlorine atom, and it is preferred that $R^4$ and $R^5$ are $C_{1-6}$ alkyl groups such as methyl group. Further, it is particularly preferred that $R^2$, $R^3$, $R^6$, and $R^7$ are hydrogen atoms, $R^4$ and $R^5$ are methyl groups, and $R^8$ represents hydroxy group.

As for the compounds wherein $R^6$ and $R^7$ are both chlorine atoms, or both fluorine atoms, for example, dihydroxy-X-xanthone synthesized from diamino-X-xanthone wherein $R^6$ and $R^7$ are both hydrogen atoms can be used in the aforementioned step (d) as a starting compound, a chlorinating agent such as NaOCl or a fluorinating agent such as Selectfluor (registered trademark) can be allowed to act on the compound to prepare a compound wherein $R^6$ and $R^7$ are both chlorine atoms or both fluorine atoms, and this compound can be reacted as a starting compound with a halogenated benzene derivative to prepare a compound of the general formula (I) wherein $R^6$ and $R^7$ are both chlorine atoms, or both fluorine atoms. As the chlorinating agent, besides NaOCl, chlorine, tert-butyl hypochlorite, N-chlorosuccinimide, N-chlorodimethylamine, chloramine T, and the like can be used. As the fluorinating agent, N-fluorobenzenesulfonimide, 1-fluoro-2,4,6-trimethylpyridinium trifluoromethanesulfonate, 1,1'-difluoro-2,2'-bipyridinium bis(tetrafluoroborate), and the like can be used.

2,7-Substituted or 2,7-unsubstituted 4,6-dichloro-3,6-dihydroxyxanthone and 2,7-substituted or 2,7-unsubstituted 4,5-difluoro-3,6-dihydroxyxanthone prepared by reacting 2,7-substituted or 2,7-unsubstituted 3,6-dihydroxyxanthone with the aforementioned chlorinating agent or fluorinating agent are novel compounds, and they are useful as synthetic intermediates for preparation of 2,7-substituted or 2,7-unsubstituted 4,5-dichloro-3,6-dihydroxyxanthen-9-yl or a salt thereof and 2,7-substituted or 2,7-unsubstituted 4,5-difluoro-3,6-dihydroxyxanthen-9-yl or a salt thereof to which a substituted phenyl group binds at the 9-position. By protecting the hydroxy group at the 3- and 6-positions of 2,7-substituted or 2,7-unsubstituted 4,5-dichloro-3,6-dihydroxyxanthone, or 2,7-substituted or 2,7-unsubstituted 4,5-difluoro-3,6-dihydroxyxanthone with protective groups, reacting the protected compound with a halogenated benzene derivative, and then performing deprotection of the hydroxy groups, 2,7-substituted or 2,7-unsubstituted 4,5-dichloro-3,6-dihydroxyxanthen-9-yl, or 2,7-substituted or 2,7-unsubstituted 4,5-difluoro-3,6-dihydroxyxanthen-9-yl, to which a substituted phenyl group binds at the 9-position, can be prepared.

The compounds represented by the general formula (IV) can be reacted with various halogenated benzene derivatives to prepare the compounds of the present invention represented by the general formula (I) introduced with various substituents on the benzene ring on which $R^1$ substitutes, and therefore they are especially useful as synthetic intermediates. Although the aforementioned preparation steps (a) to (f) are specifically described in the examples, it should be understood that such preparation methods further appropriately modified and improved by those skilled in the art on the basis of their usual knowledge are also encompassed by the scope of the present invention. Methods comprising any one of the steps (a) to (e), or two or more continuous steps among them are also encompassed by the scope of the present invention.

In the compounds represented by the general formula (IV), type of the protective group of the phenolic hydroxy group as $R^{13}$ is not particularly limited, and it can be appropriately selected from, for example, t-butyldimethylsilyl group, methyl group, methoxymethyl group, t-butyl group, and the like. About the protective group of phenolic hydroxy group, for example, T. W. Greene, Protective Groups in Organic Synthesis, John Wiley & Sons, Inc. (1981), and the like can be referred to.

EXAMPLES

Hereafter, the present invention will be more specifically explained with reference to examples. However, the scope of the present invention is not limited by the following examples.

Example 1

The compound of the present invention was synthesized according to the following scheme.

[Formula 13]

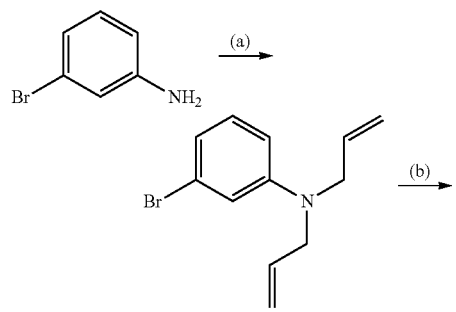

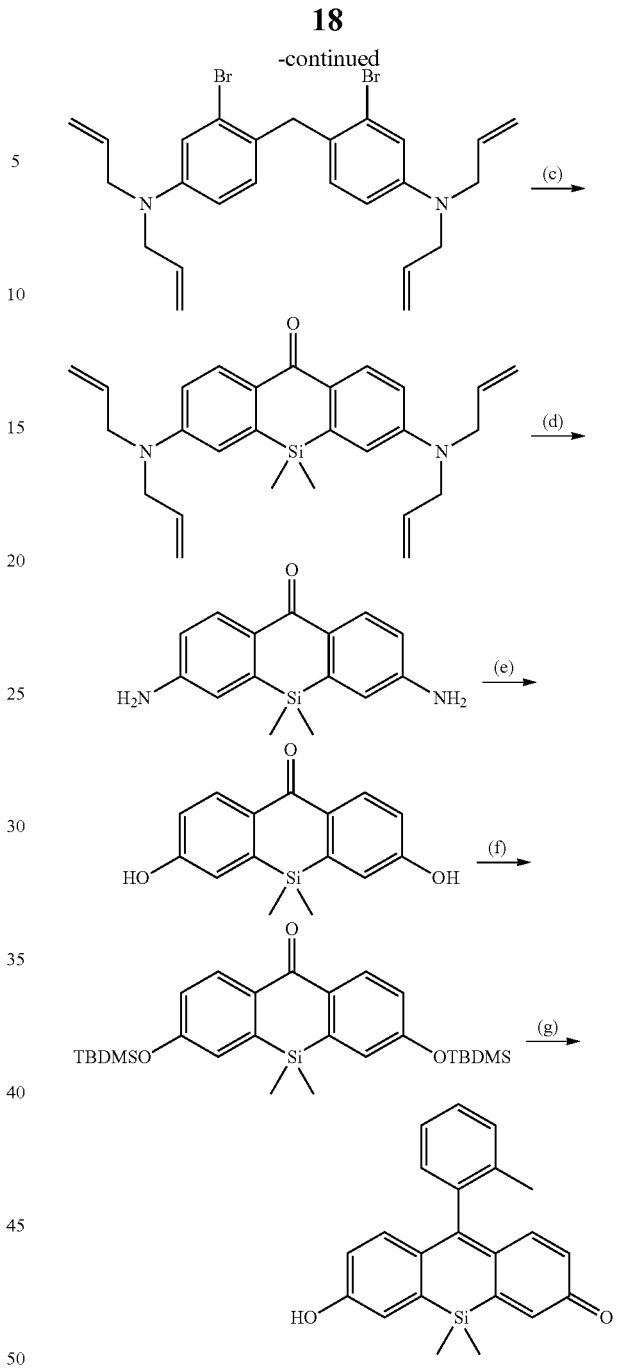

(a) 3-Bromo-N,N-diallylaniline $K_2CO_3$ (22.0 g, 159 mmol) was suspended in acetonitrile, the suspension was added with 3-bromoaniline (8.71 mL, 80.0 mmol) and allyl bromide (23.7 mL, 280 mmol), and the mixture was stirred at 80° C. for 14 hours. The reaction mixture was cooled to room temperature, then filtered through Celite, and sufficiently washed with ethyl acetate. The solvent was removed, and then the residue was purified by column chromatography (silica gel, ethyl acetate/hexane (1/40)) to obtain 3-bromo-N,N-diallylaniline (17.1 g, 67.9 mmol, yield 85%).

$^1$H-NMR (300.40 MHz, CDCl$_3$): δ 3.87-3.90 (m, 4H), 5.11-5.15 (m, 2H), 5.17-6.18 (m, 2H), 5.75-5.88 (m, 2H), 6.58 (dd, 1H, J=2.2, 8.1 Hz), 6.77-6.81 (m, 2H), 7.01 (t, 1H, J=8.1 Hz)

$^{13}$C-NMR (75.45 MHz, CDCl$_3$): δ 52.7, 110.8, 115.0, 116.3, 119.0, 123.3, 130.2, 133.2, 150.0

HRMS (ESI+): Found 252.0429. calculated 252.0388 for [M+H]$^+$ (4.1 mmu).

(b) Bis(2-bromo-4-N,N-diallylaminophenyl)methane

3-Bromo-N,N-diallylaniline (17.1 g, 67.9 mmol) was dissolved in acetic acid (200 mL), the solution was added with a 37% formaldehyde solution (10.2 g, 340 mmol), and the mixture was heated at 80° C. for 75 minutes. The reaction mixture was cooled to room temperature, and then neutralized with saturated aqueous NaHCO$_3$ and NaOH. This mixture was extracted with dichloromethane, and the organic layer was washed with brine. The organic layer was dried over Na$_2$SO$_4$, the solvent was removed, and then the residue was purified by column chromatography (silica gel, ethyl acetate/hexane (1/30)) to obtain bis(2-bromo-4-N,N-diallylaminophenyl)methane (15.2 g, 29.5 mmol, yield 87%).

$^1$H-NMR (300.40 MHz, CDCl$_3$): δ 3.85-3.87 (m, 8H), 3.96 (s, 2H), 5.13-5.19 (m, 8H), 5.76-5.88 (m, 4H), 6.54 (dd, 2H, J=2.9, 8.8 Hz), 6.81 (d, 2H, J=8.1 Hz), 6.90 (d, 2H, J=2.9 Hz)

$^{13}$C-NMR (75.45 MHz, CDCl$_3$): δ 39.7, 52.7, 111.7, 116.0, 116.2, 126.5, 126.9, 130.8, 133.5, 148.1

HRMS (ESI+): Found 517.0654. calculated 517.0677 for [M+H]$^+$ (−2.3 mmu).

(c) N,N,N',N'-Tetraallyl-diamino-Si-xanthone

Bis(2-bromo-4-N,N-diallylaminophenyl)methane (8.16 g, 15.8 mmol) and anhydrous tetrahydrofuran (THF, 50 mL) were put into a dried flask inside of which was substituted with argon. The mixture was cooled to −78° C., and then added with 1 M sec-butyllithium (45 mL, 45 mmol), and the mixture was stirred for 20 minutes. The mixture was slowly added with dichlorodimethylsilane (2.9 mL, 30 mmol) dissolved in anhydrous THF (10 mL) at the same temperature, and the mixture was returned to room temperature, and stirred for 1 hour. The reaction was terminated with 2 N hydrochloric acid, and the reaction mixture was neutralized with NaHCO$_3$. This mixture was extracted with dichloromethane, the organic layer was washed with brine, and dried over Na$_2$SO$_4$, and then the solvent was removed. The residue was dissolved in acetone (150 mL), the solution was cooled to 0° C. and added portionwise with KMnO$_4$ (6.88 g, 43.5 mmol) over 2 hours, and the mixture was further stirred at the same temperature for 1 hour. The mixture was added with dichloromethane (200 mL), and the mixture was subjected to suction filtration using filter paper. The solvent was removed, and the residue was purified by column chromatography (silica gel, dichloromethane) to obtain N,N,N',N'-tetraallyl-diamino-Si-xanthone (2.23 g, 5.20 mmol, yield 330).

$^1$H-NMR (300.40 MHz, CDCl$_3$): δ 0.41 (s, 6H), 4.02 (d, 8H, J=5.1 Hz), 5.17-5.23 (m, 8H), 5.82-5.94 (m, 4H), 6.80-6.83 (m, 4H), 8.34 (d, 2H, J=8.1 Hz)

$^{13}$C-NMR (75.46 MHz, CDCl$_3$): δ −1.1, 52.8, 113.5, 114.8, 116.7, 130.0, 131.7, 133.1, 140.5, 150.2, 185.1

HRMS (ESI+): Found 429.2347. calculated 429.2362 for [M+H]$^+$ (−1.5 mmu).

(d) Diamino-Si-xanthone

Pd(PPh$_3$)$_4$ (35.0 mg, 0.0303 mmol) and 1,3-dimethylbarbituric acid (196 mg, 1.08 mmol) were put into a dried flask inside of which was substituted with argon. The mixture was added with N,N,N',N'-tetraallyl-diamino-Si-xanthone (99.2 mg, 0.231 mmol) dissolved in dichloromethane (10 mL), and the mixture was stirred at 64° C. for 16 hours. The solvent was removed, the residue was suspended in saturated aqueous Na$_2$CO$_3$, and the suspension was extracted with dichloromethane. The organic layer was dried over Na$_2$SO$_4$, the solvent was removed, and then the residue was purified by column chromatography (silica gel, ethyl acetate/hexane (4/3)) to obtain diamino-Si-xanthone (48.8 mg, 0.182 mmol, yield 79%).

$^1$H-NMR (300.40 MHz, CD$_3$OD): δ 0.40 (s, 6H), 6.76 (dd, 2H, J=2.6, 8.4 Hz), 6.88 (d, 2H, J=2.2 Hz), 8.13 (d, 2H, J=8.8 Hz)

$^{13}$C-NMR (75.46 MHz, CD$_3$OD): δ −1.3, 116.6, 118.4, 131.0, 132.8, 142.6, 153.0, 187.5

HRMS (ESI+Tof): m/z Found 269.1108. calculated 269.1110 for [M+H]$^+$ (−0.2 mmu).

(e) Dihydroxy-Si-xanthone

Diamino-Si-xanthone (48.8 mg, 0.182 mmol) was dissolved in a mixed solvent (methanol, 6 N H$_2$SO$_4$, 4/5, 45 mL). The solution was cooled to 0° C., and then slowly added with NaNO$_2$ (84.6 mg, 1.22 mmol) dissolved in water (2 mL), and the mixture was stirred at the same temperature for 1 hour. This mixture was slowly added to boiling 1 N H$_2$SO$_4$ (50 mL), and the mixture was further refluxed for 10 minutes, and then cooled on ice. The reaction mixture was extracted with dichloromethane, and the organic layer was sufficiently washed with brine. The organic layer was dried over Na$_2$SO$_4$, the solvent was removed, and then the residue was purified by column chromatography (silica gel, methanol/dichloromethane (1/20)) to obtain dihydroxy-Si-xanthone (32.9 mg, 0.122 mmol, yield 67%).

$^1$H-NMR (300.40 MHz, CD$_3$OD): δ 0.45 (s, 6H), 6.95 (dd, 2H, J=2.2, 8.8 Hz), 7.07 (d, 2H, J=2.2 Hz), 8.26 (d, 2H, J=8.8 Hz)

$^{13}$C-NMR (75.45 MHz, CD$_3$OD): δ −1.5, 118.4, 120.0, 133.3, 133.8, 143.1, 162.2, 187.6

HRMS (ESI-Tof): Found 269.0674. calculated 269.0634 for [M−H]$^−$ (4.0 mmu).

(f) 3,6-Di-tert-butyldimethylsilyloxy-Si-xanthone

Dihydroxy-Si-xanthone (32.9 mg, 0.122 mmol) and imidazole (85.5 mg, 1.26 mmol) were dissolved in dichloromethane (20 mL), the solution was slowly added with tert-butyldimethylsilyl chloride (185 mg, 1.23 mmol) dissolved in dichloromethane (5 mL), and the mixture was stirred at room temperature for 14 hours. The mixture was added with water, the mixture was extracted with dichloromethane, and the organic layer was washed with brine. The organic layer was dried over Na$_2$SO$_4$, the solvent was removed, and then the residue was purified by column chromatography (silica gel, ethyl acetate/hexane (1/20)) to obtain 3,6-di-tert-butyldimethylsilyloxy-Si-xanthone (52.8 mg, 0.106 mmol, yield 84%).

$^1$H-NMR (300.40 MHz, CDCl$_3$): δ 0.26 (s, 12H), 0.46 (s, 6H), 1.01 (s, 18H), 6.98 (dd, 2H, J=2.2, 8.8 Hz), 7.04 (d, 2H, J=2.9 Hz), 8.37 (d, 2H, J=8.8 Hz)

$^{13}$C-NMR (75.45 MHz, CDCl$_3$): δ −4.3, −1.6, 18.3, 25.6, 121.8, 123.7, 132.3, 134.5, 141.1, 158.7, 186.0

HRMS (ESI+): Found 499.2480. calculated 499.2620 for [M+H]$^+$ (−4.0 mmu).

(g) Synthesis of 2-Me TokyoMagenta

2-Bromotoluene (200 μL, 1.6 mmol) and anhydrous THF (5 mL) were put into a sufficiently dried flask inside of which was substituted with argon. The mixture was cooled to −78° C., and then added with 1 M sec-butyllithium (1.0 mmol), and the mixture was stirred for 20 minutes. The mixture was slowly added with 3,6-di-tert-butyldimethylsilyloxy-Si-xanthone (9.4 mg, 0.019 mmol) dissolved in anhydrous THF (5 mL) at the same temperature, and the mixture was returned to room temperature. The mixture was stirred at room temperature for 1 hour, and then added with 2 N HCl (10 mL), and the mixture was stirred for 20 minutes. This mixture was extracted with dichloromethane, and the organic layer was washed with brine. The organic layer was dried over $Na_2SO_4$, the solvent was removed, and then the residue was purified by HPLC to obtain 2-Me TokyoMagenta (4.5 mg, 0.013 mmol, yield 69%).

$^1$H-NMR (300.40 MHz, $CD_3OD$): δ 0.46 (s 6H), 2.01 (s, 3H), 6.33 (dd, 2H, J=2.9, 9.5 Hz), 7.01-7.09 (m, 5H), 7.27-7.46 (m, 3H)

HRMS (ESI−): Found, 343.1120. calculated 343.1154 for [M−H]− (−3.41 mmu).

(h) Synthesis of 2-Me TokyoMagenta βgal

[Formula 14]

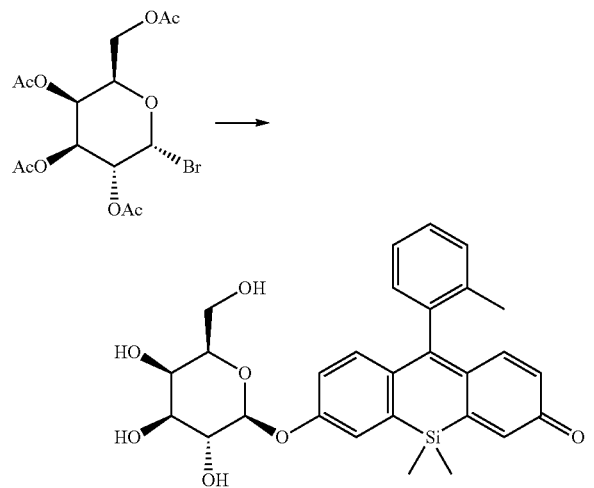

2-Me TokyoMagenta (4.6 mg, 0.013 mmol), 2,3,4,6-tetra-O-acetyl-α-galactopyranosyl bromide (80.8 mg, 0.197 mmol) and $Cs_2CO_3$ (29.6 mg, 0.0909 mmol) were added to acetonitrile (3 mL), and the mixture was stirred overnight at room temperature under an argon-substituted atmosphere. The mixture was filtered, and the solvent of the filtrate was removed. The residue was dissolved in methanol (3 mL), the solution was cooled to 0° C., and slowly added with 15 μL of a 28% solution of sodium methoxide in methanol, and then this mixture was stirred for 1 hour. The reaction was terminated with 0.2 N aqueous HCl, and the reaction mixture was extracted with dichloromethane. The organic layer was washed with brine, and dried over $Na_2SO_4$ and the solvent was removed. The residue was purified by HPLC to obtain 2-Me TokyoMagenta βgal (2.4 mg, 0.0047 mmol, yield 36%).

$^1$H-NMR (300.40 MHz, $CD_3$ OD): δ 0.51 (d, 3H, J=1.8 Hz), 0.52 (d, 3H J=1.8 Hz), 2.04 (s, 3H), 3.59 (dd, 1H, J=3.7, 9.5 Hz), 3.69-3.89 (m, 5H), 4.98 (dd, 1H, J=3.3, 7.7 Hz), 6.23 (dd, 1H, J=2.2, 10.3 Hz), 6.87-6.91 (m, 2H), 6.98-7.13 (m, 3H), 7.33-7.46 (m, 3H), 7.50 (d, 1H, J=2.2 Hz)

HRMS (ESI$^+$): m/z Found 507.1826. calculated 507.1839 for [M+H]$^+$ (−1.3 mmu).

Example 2

Absorption and fluorescence profiles of 2-Me TokyoMagenta obtained in the step (g) mentioned above were measured at various pH values. The results are shown in FIG. 1. It was confirmed that, with the shift of pH from the acidic side to the alkaline side, the maximal absorption wavelength shifted to the longer wavelength side from around 471 nm to around 582 nm (FIG. 1, upper graph), and that fluorescence emission with excitation light of 550 nm significantly increased (FIG. 1, lower graph). It is considered that 2-Me TokyoMagenta exists in an equilibrated state of the non-dissociated form (neutral form) and the dissociated form (anion form) mentioned below depending on pH. It was found that the fluorescence profiles of the compounds were significantly different from each other, for example, the absorption spectrum of the dissociated form shifts to the longer wavelength side compared with the non-dissociated form, absorption coefficients and fluorescence quantum yields of them are different, and the like.

[Formula 15]

|  | ε | $Φ_{fl}$ |
|---|---|---|
| Anion form | 110000 | 0.42 |
| Neutral form | 29000 | 0.10 |

Figure 2:
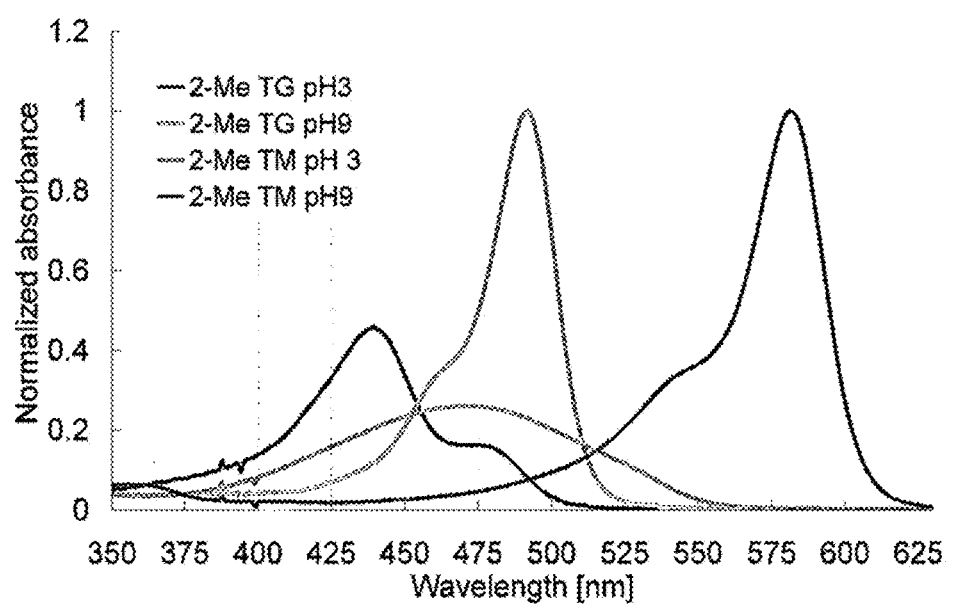
FIG. 2 shows results of comparison of absorption wavelengths of 2-Me TokyoMagenta, which is a typical example of the compound of the present invention, and 2-Me TokyoGreen (9-(2'-methylphenyl)-xanthen-3-one) having an oxygen atom at the 10-position of the xanthene ring.

The results of comparison of the absorption wavelengths of 2-Me TokyoMagenta and 2-Me TokyoGreen (9-(2'-methylphenyl)-xanthen-3-one) having oxygen atom at the 10-position of the xanthene ring are shown in FIG. 2 and Table 1. The measurement was performed at pH 3 and 9 in a sodium phosphate buffer. As a result, it was demonstrated that 2-Me TokyoMagenta showed a larger absorption wavelength change with change of pH compared with 2-Me TokyoGreen (in Table 1, Neutral form corresponds to pH 3, and Anion form corresponds to pH 9).

TABLE 1

| λmax | 2-Me TokyoGreen | 2-Me TokyoMagenta |
|---|---|---|
| Anion form | 492 | 582 |
| Neutral form | 439 | 471 |

Example 3

Figure 3:
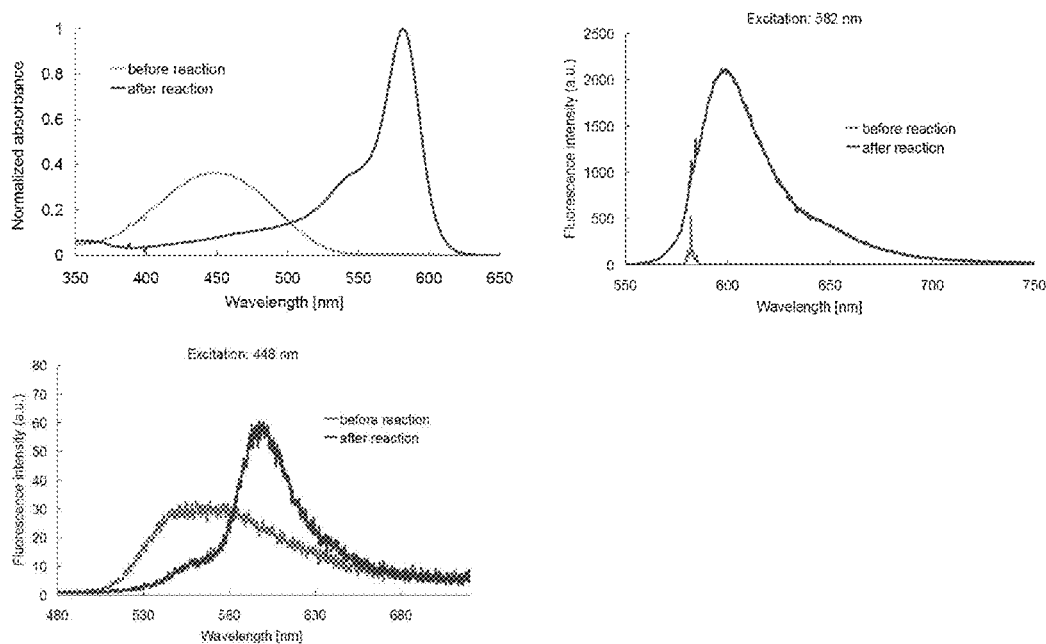
FIG. 3 shows absorption spectra (upper left graph), and fluorescence spectra (upper right graph (excitation wavelength, 682 nm) and lower left graph (excitation wavelength, 448 nm) of 2-Me TokyoMagenta βgal, designed as a fluorescent probe for measurement of β-galactosidase. The spectra were measured before and after a treatment with an enzyme.

The characteristics of 2-Me TokyoMagenta βgal, which was designed as a fluorescent probe for β-galactosidase measurement, as an enzyme substrate and a fluorescent probe were evaluated. There are shown absorption spectra (FIG. 3, upper left graph) and fluorescence spectra (FIG. 3, upper right graph (excitation wavelength, 582 nm) and FIG. 3, lower left graph (excitation wavelength, 448 nm)) of 2-Me TokyoMagenta βgal measured before and after a treatment with β-galactosidase (6 units) in a 0.1 M sodium phosphate buffer (pH 7.0) containing 0.1% dimethyl sulfoxide. The λmax values measured before and after the reaction were 448 nm (before the reaction), and 582 nm (after the reaction), respectively.

Figure 4:
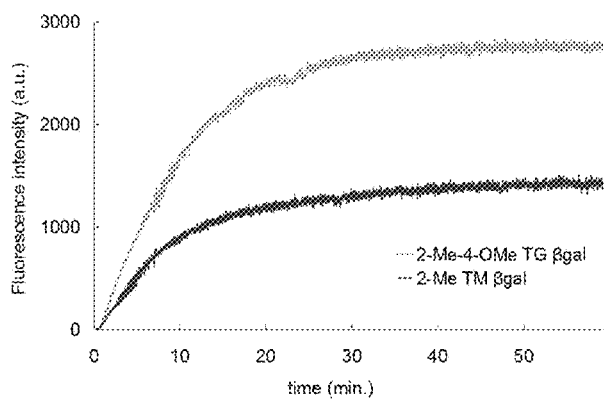
FIG. 4 shows results of measurement of fluorescence intensity over time, indicating advance of the hydrolysis reaction of 2-Me TokyoMagenta βgal with β-galactosidase. As a control, 2-Me-4-OMe TokyoGreen βgal was used, which had been already widely used as a fluorescent probe for β-galactosidase measurement.

Advance of the hydrolysis reaction of 2-Me TokyoMagenta βgal by β-galactosidase was monitored by periodically measuring fluorescence intensity. As a control, 2-Me-4-OMe TokyoGreen βgal (9-(4'-methoxy-2'-methylphenyl)-6-(β-D-galactopyranosyloxy)-xanthen-3-one), which had been already widely used as a fluorescent probe for β-galactosidase measurement, was used. The reaction was performed at 37° C. in a 0.1 M sodium phosphate buffer (pH 7.4) containing 1 μM 2-Me TokyoMagenta βgal or 2-Me-4-OMe TokyoGreen βgal and 0.1% dimethyl sulfoxide. One unit (1.3 μg) of β-galactosidase was added 40 seconds afterward. The results are shown in FIG. 4. As shown in the following scheme, fluorescence was generated by cancellation of PET in the case of 2-Me-4-OMe 4-TokyoGreen βgal, and increase of fluorescence intensity due to red shift was observed in the case of 2-Me TokyoMagenta βgal.

[Formula 16]

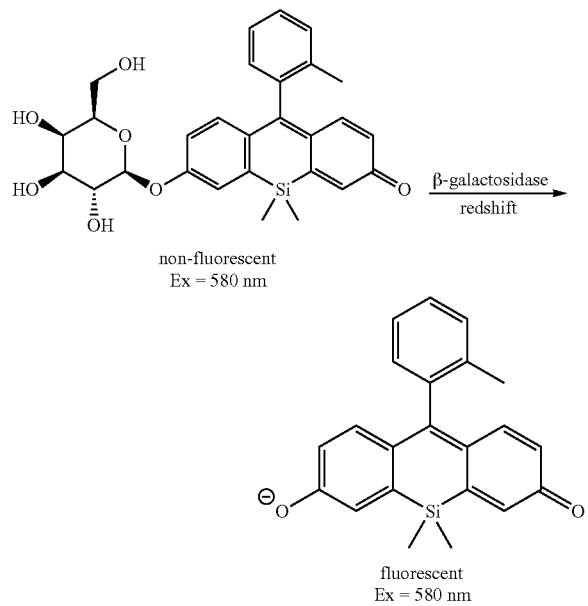

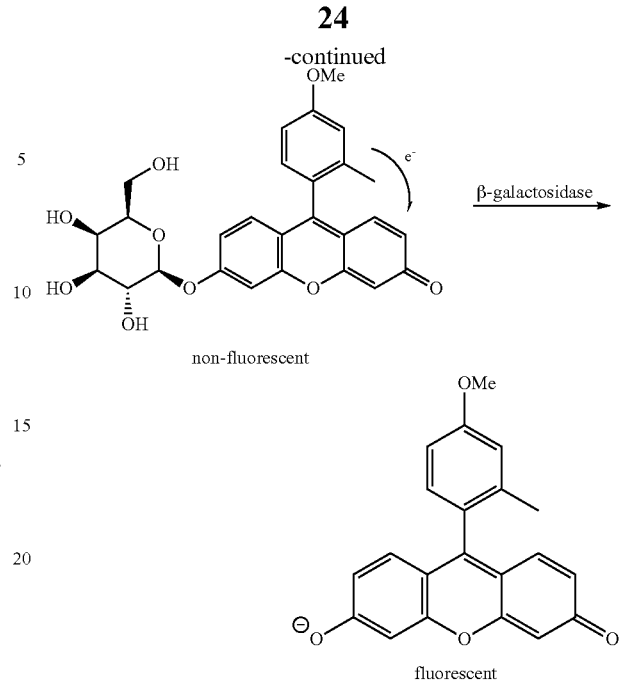

Example 4

Figure 5:
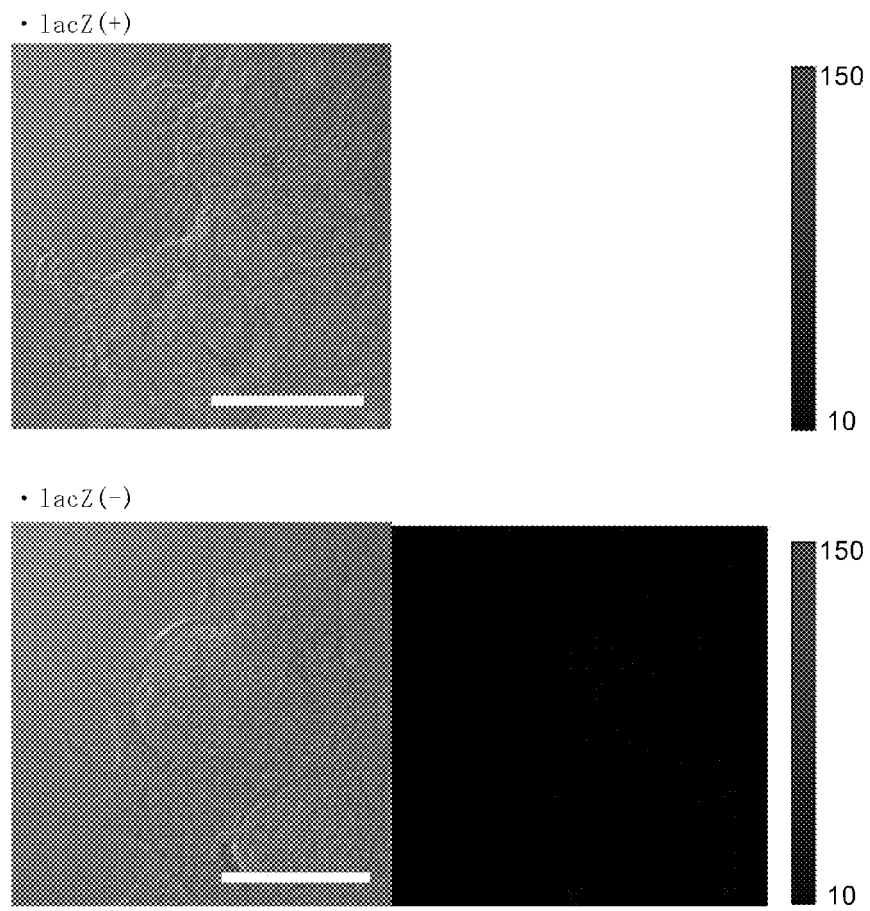
FIG. 5 shows results of measurement of intracellular β-galactosidase using 2-Me TokyoMagenta βgal as a fluorescent probe. The bars shown in the photographs indicate 30 μm.

2-Me TokyoMagenta βgal was introduced into cells, and it was confirmed that it functioned as a fluorescent probe for β-galactosidase measurement. The HEK293 cells (lacZ(+) or lacZ(−)) were incubated with 10 μM 2-Me TokyoMagenta βgal at 37° C. for 30 minutes in the Dulbecco's modified Eagle medium (DMEM) containing 0.1% dimethyl sulfoxide, and fluorescence spectrum was measured with an excitation wavelength of 580 nm and detection wavelength of 600 to 620 nm. The results are shown in FIG. 5. In the lacZ(+) cells, fluorescence emitted by the fluorescent probe hydrolyzed by β-galactosidase was confirmed, whereas fluorescence was not observed in the lacZ(−) cells. On the basis of this result, it is clear that 2-Me TokyoMagenta βgal introduced into cells functions as a fluorescent probe for β-galactosidase measurement.

Example 5

By using 3,6-di-tert-butyldimethylsilyloxy-Si-xanthone obtained in Example 1, the step (f), Compounds (A) to (E) of the present invention were synthesized by the following procedures.

A bromobenzene derivative (1.0 mmol) and anhydrous tetrahydrofuran (THF, 5 mL) were put into a sufficiently dried flask inside of which was substituted with argon. The mixture was cooled to −78° C., and then added with 1 M sec-butyllithium (0.5 mmol), and the mixture was stirred for 20 minutes. The mixture was slowly added with 3,6-di-tert-butyldimethylsilyloxy-Si-xanthone (0.015 to 0.019 mmol) dissolved in anhydrous THF (5 mL) at the same temperature, and the mixture was returned to room temperature. The mixture was stirred at room temperature for 1 hour, and then added with 2 N HCl (5 mL), and the mixture was stirred for 20 minutes. The reaction mixture was extracted with dichloromethane, and the organic layer was washed with brine, and dried over anhydrous sodium sulfate. The solvent was removed, and then the residue was purified by HPLC to obtain the objective substance.

(a) 2,4-Dimethyl TokyoMagenta (Compound (A))

[Formula 17]

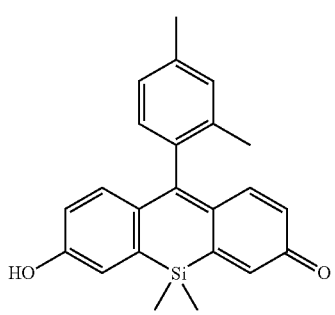

Yield: 93%

¹H-NMR (300 MHz, D₂O): δ 0.37 (s, 6H), 1.83 (s, 3H), 2.25 (s, 3H), 6.21 (dd, 2H, J=1.5, 9.5 Hz), 6.75 (d, 1H, J=8.1 Hz), 6.89-6.94 (m, 5H), 7.07 (s, 1H)

(b) 2,5-Dimethyl TokyoMagenta (Compound (B))

[Formula 18]

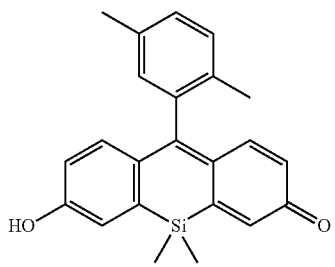 [SMILES: Cc1ccccc1C1=C2C=CC(=O)C=C2[Si](C)(C)c2cc(O)ccc21]

Yield: 96%

¹H-NMR (300 MHz, D₂O): δ 0.38, (s, 3H), 0.40, (s, 3H), 1.82 (s, 3H), 2.10 (s, 3H), 6.19 (dd, 2H, J=2.2, 9.5 Hz), 6.73 (s, 1H), 6.89-7.11 (m, 6H)

(c) 2-Methoxy TokyoMagenta (Compound (C))

[Formula 19]

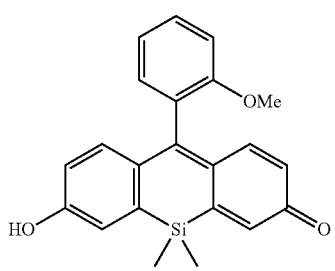

Yield: 88%

¹H-NMR (300 MHz, D₂O): δ 0.40, (s, 3H), 0.44, (s, 3H), 3.65 (s, 3H), 6.29 (dd, 2H, J=2.9, 9.5 Hz), 6.96-7.18 (m, 70, 7.560 (dd, 1H, J=7.0, 7.0 Hz)

(d) 2-Methoxy-5-methyl TokyoMagenta (Compound (D))

[Formula 20]

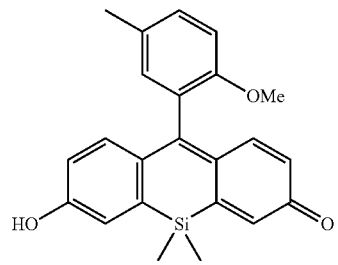

Yield: 99%

¹H-NMR (300 MHz, D₂O): δ 0.40, (s, 3H), 0.42, (s, 3H), 2.11 (s, 3H), 3.58 (s, 3H), 6.23 (dd, 2H, J=2.2, 9.5 Hz), 6.75 (s, 1H), 6.95-7.03 (m, 5H), 7.21 (d, 1H, J=8.1 Hz)

(e) 2,5-Dimethoxy TokyoMagenta (Compound (E))

[Formula 21]

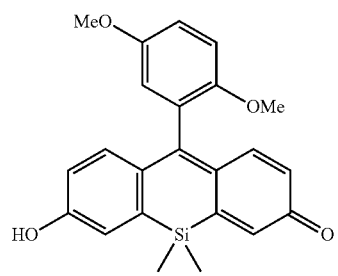

Yield: 90%

¹H-NMR (300 MHz, D₂O): δ 0.39, (s, 3H), 0.41, (s, 3H), 3.53 (s, 3H), 3.58 (s, 3H), 6.22 (dd, 2H, J=2.2, 9.5 Hz), 6.54 (d, 1H, J=2.9 Hz), 6.89-7.02 (m, 6H)

Example 6

Figure 6:
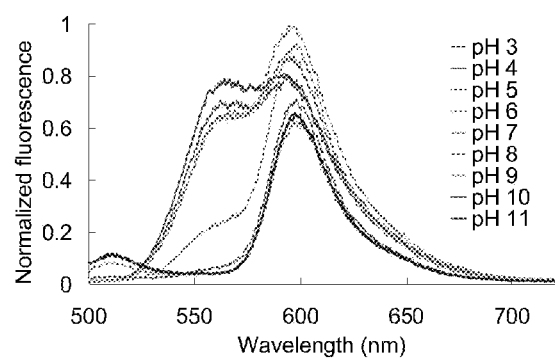
FIG. 6 shows results of measurement of fluorescence spectra of 2-Me TokyoMagenta, which is a typical example of the compound of the present invention. The measurement was performed with changing pH (excitation wavelength, 471 nm) by using a 1 μM solution of 2-Me TokyoMagenta dissolved in a 0.1 M phosphate buffer containing 1% dimethyl sulfoxide (DMSO).
Figure 7:
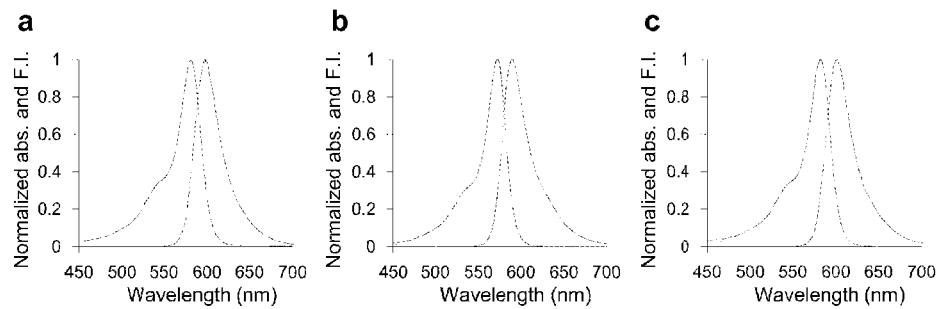
FIG. 7 shows absorption and fluorescence spectra of 2-Me TM (a), 2-Me Ge-TM (b), and 2-Me DiEtTM (c). The measurement was performed at pH 9.
Figure 8:
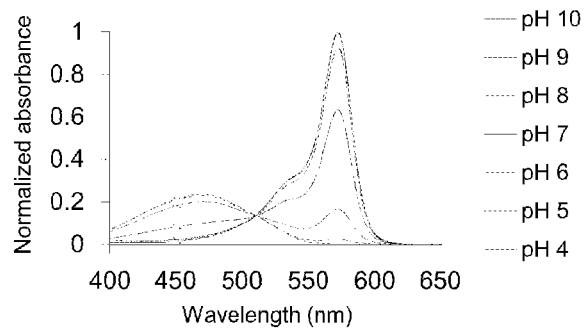
FIG. 8 shows pH-dependent change of absorption spectrum of 2-Me Ge-TM (concentration was 1 μM in a 0.1 M phosphate buffer containing 1% DMSO).
Figure 9:
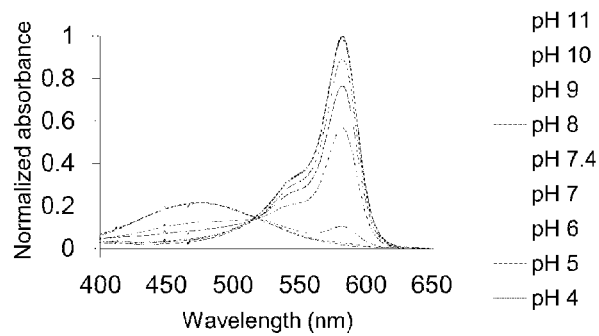
FIG. 9 shows pH-dependent change of absorption spectrum of 2-Me DiEtTM (concentration was 1 μM in a 0.1 M phosphate buffer containing 1% DMSO).
Figure 10:
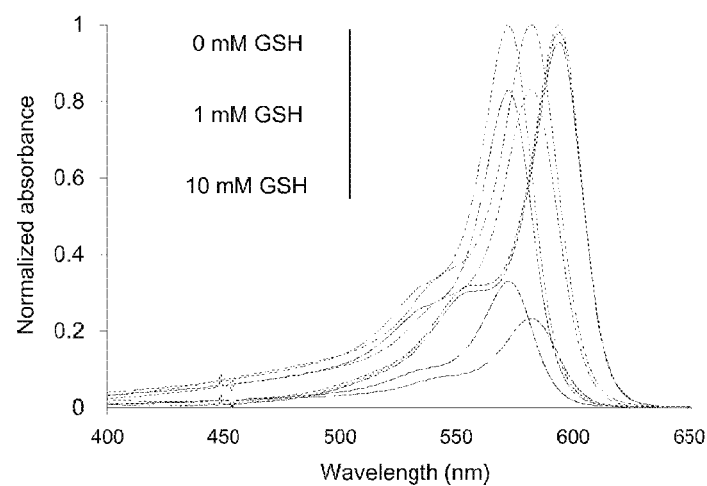
FIG. 10 shows reactivity of 2-Me Ge-TM (blue), 2-Me TM (green) and 2-Me DCTM (red) with GSH in a phosphate buffer (pH 7.4) containing 1% DMSO.
Figure 11:
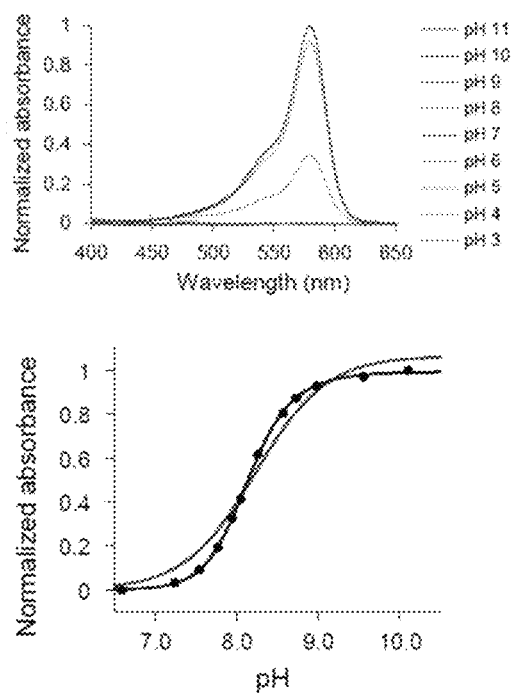
FIG. 11 The upper graph shows pH-dependent change of absorption spectrum of 2-COOH TM (concentration was 1 μM in a 0.1 M phosphate buffer containing 1% DMSO), and the lower graph shows pH-dependent change of absorption spectrum of 2-COOH TM at 580 nm. Curve fitting was performed on the basis of single-phase normalization (red) and two-phase normalization (blue), and $X^2$ values were 0.041 and $4.4*10^{-4}$, respectively.
Figure 12:
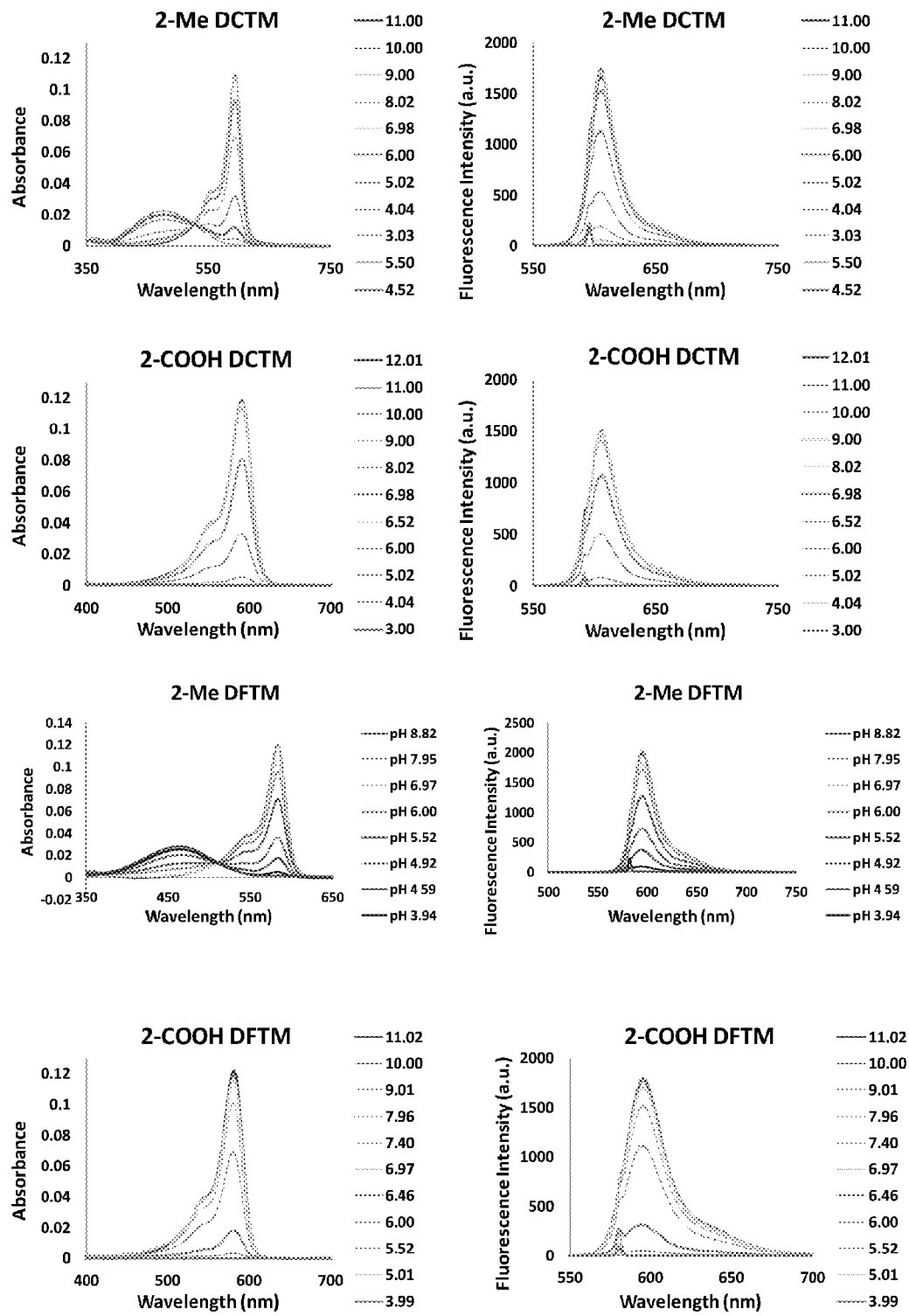
FIG. 12 shows optical characteristics of 2-MeDCTM, 2-COOH DCTM, 2-Me DFTM, and 2-COOH DFTM, and shows pH-dependent change of absorption spectrum (let) and change of fluorescence (right) at a concentration of 1 μM in a 0.1 M phosphate buffer containing 1% DMSO.

Absorption and fluorescence profiles of 2-Me TokyoMagenta obtained in the step (g) mentioned above were measured at various pH values (excitation wavelength, 471 nm). The results are shown in FIG. 6. It was confirmed that, with the shift of pH from the acidic side to the alkaline side, fluorescence intensity decreased around 590 nm, and fluorescence intensity increased around 560 nm. It is considered that 2-Me TokyoMagenta exists in an equilibrated state of the non-dissociated form (neutral form) and the dissociated form (anion form) mentioned below depending on pH, and it was found that the fluorescence spectra of the dissociated form and the non-dissociated form observed with the excitation wavelength of 471 nm were significantly different from each other.

Example 7

A germanium-containing compound was synthesized by the following procedures.

[Formula 22]

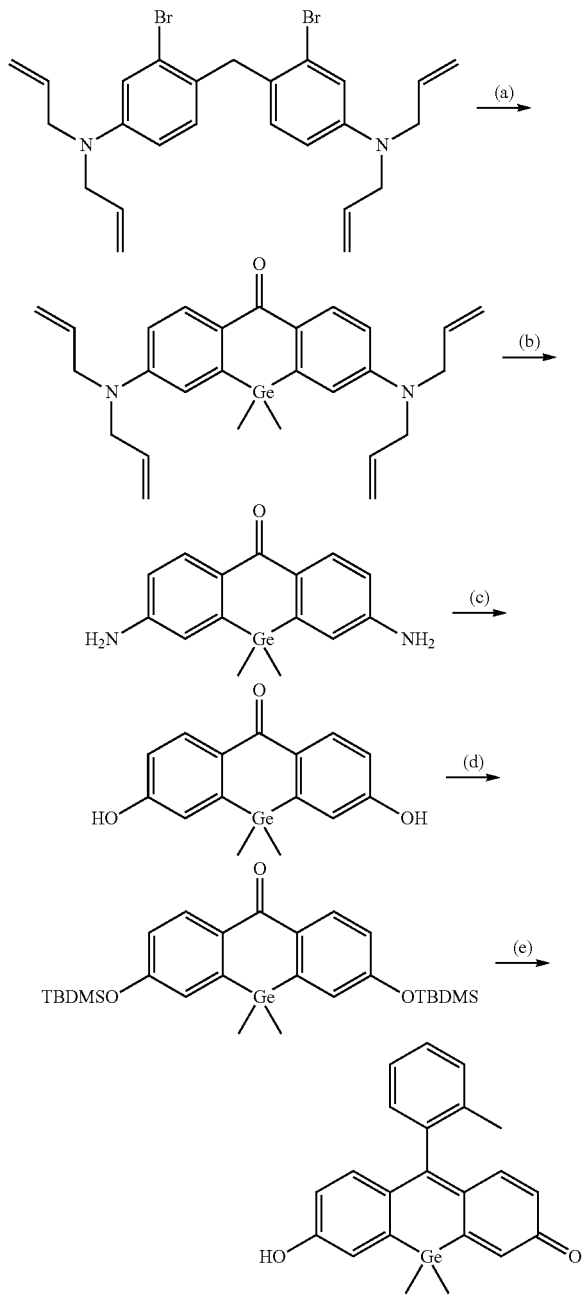

(a) N,N,N',N'-3,6-Tetraallyldiamino-Ge-xanthone

Bis(2-bromo-4-N,N-diallylaminophenyl)methane (6.16 g, 11.9 mmol) and anhydrous THF (40 mL) were put into a dried flask inside of which was substituted with argon. The mixture was cooled to −78° C., and then added with 1 M sec-butyllithium (BuLi, 34 mL, 34 mmol), and the mixture was stirred for 20 minutes. The mixture was slowly added with $GeMe_2Cl_2$ (2.62 mL, 22.7 mmol) dissolved in anhydrous THF (15 mL) at the same temperature, and the mixture was returned to room temperature, and stirred for 1 hour. The reaction was terminated with 2 N HCl, and the reaction mixture was neutralized with $NaHCO_3$. This mixture was extracted with dichloromethane, the organic layer was washed with brine, and dried over $Na_2SO_4$, and then the solvent was removed. The residue was dissolved in acetone (120 mL), and the solution was cooled to 0° C. The solution was added portionwise with $KMnO_4$ (5.20 g, 32.9 mmol) over 2 hours, and the mixture was further stirred at the same temperature for 1 hour. The mixture was added with dichloromethane (200 mL), and the mixture was subjected to suction filtration using filter paper. Then, the solvent was removed, and the residue was purified by column chromatography (silica gel, dichloromethane) to obtain the objective substance (1.29 g, 2.72 mmol, yield 23%).

$^1$H NMR (300 MHz, $CDCl_3$): δ 0.54 (s, 6H), 4.00-4.02 (m, 8H) 5.17-5.23 (m, 8H), 5.81-5.94 (m, 4H), 6.72 (d, 2H, J=2.9 Hz), 6.78 (dd, 2H, J=2.6, 9.2 Hz), 8.36 (d, 2H, J=8.8 Hz)

$^{13}$C NMR (75 MHz, $CDCl_3$): δ −1.8, 52.3, 112.6, 114.4, 116.2, 129.6, 131.7, 132.7, 142.8, 149.8, 184.6

LRMS (ESI$^+$): m/z Found 475. calculated 475 for $[M+H]^+$.

(b) 3,6-Dihydroxy-Ge-xanthone $Pd(PPh_3)_4$ (330 mg, 0.285 mmol) and 1,3-dimethylbarbituric acid (1.41 g, 9.04 mmol) were put into a dried flask inside of which was substituted with argon. The mixture was added with N,N,N',N'-tetraallyldiamino-Ge-xanthone (1.00 g, 2.11 mmol) dissolved in dichloromethane (50 mL), and the mixture was stirred at 35° C. for 16 hours. The solvent was removed, the residue was suspended in saturated aqueous $Na_2CO_3$, and the suspension was extracted with dichloromethane. The organic layer was dried over $Na_2SO_4$, the solvent was removed, and then the residue was purified by column chromatography (silica gel, ethyl acetate/hexane (4/3)) to obtain a 3,6-diamino-Ge-xanthone mixture (760 mg, quantum yield).

$^1$H NMR (300 MHz, $CD_3OD$): δ 0.55 (s, 6H), 6.73-6.76 (m, 4H), 8.33 (d, 2H, J=9.5 Hz)

$^{13}$C NMR (75 MHz, $CD_3OD$): δ −1.9, 116.1, 118.3, 130.9, 133.2, 145.2, 152.9, 187.3

LRMS (ESI$^+$): m/z Found 315. calculated 315 for $[M+H]^+$.

(c) 3,6-Dihydroxy-Ge-xanthone

The 3,6-diamino-Ge-xanthone mixture (760 mg) was dissolved in methanol/6 N $H_2SO_4$ (3/4, 45 mL). The solution was cooled to 0° C., and then slowly added with $NaNO_2$ (838 mg, 12.1 mmol) dissolved in $H_2O$ (5 mL), and the mixture was stirred at the same temperature for 1 hour. The mixture was slowly added to boiling 1 N $H_1SO_4$ (70 mL), and the mixture was further refluxed for 10 minutes, and then cooled on ice. The reaction mixture was extracted with dichloromethane, and the organic layer was sufficiently washed with brine. The organic layer was dried over $Na_2SO_4$, the solvent was removed, and then the residue was purified by column chromatography (silica gel, ethyl acetate/hexane (1/1)) to obtain 3,6-dihydroxy-Ge-xanthone (478 mg, 1.52 mmol, yield 56% in 2 steps).

$^1$H NMR (300 MHz, $CD_3OD$): δ 0.58 (s, 6H), 6.90 (dd, 2H, J=2.2, 8.8 Hz), 7.0 (d, 2H, J=2.2 Hz), 8.25 (d, 2H, J=8.8 Hz)

$^{13}$C NMR (75 MHz, CD$_3$OD): δ −2.0, 117.7, 120.0, 133.7, 133.8, 145.6, 162.0, 187.7

LRMS (ESI$^+$): Found 317. calculated 317 for [M+H]$^+$.

(d) 3,6-DiTBDMSO-Ge-xanthone

Dihydroxy-Ge-xanthone (478 mg, 1.52 mmol) and imidazole (1.77 g, 26.0 mmol) were dissolved in dichloromethane (150 mL), the solution was slowly added with TBDMSCl (3.70 g, 24.5 mmol) dissolved in dichloromethane (50 mL), and the mixture was stirred at room temperature for 14 hours. The mixture was added with H$_2$O, the mixture was extracted with dichloromethane, and the organic layer was washed with brine. The organic layer was dried over Na$_2$SO$_4$, the solvent was removed, and then the residue was purified by column chromatography (silica gel, ethyl acetate/hexane (1/30)) to obtain 3,6-diTBDMSO-Ge-xanthone (702 mg, 1.29 mmol, yield 85%).

$^1$H NMR (300 MHz, CDCl$_3$): δ 0.25 (s, 12H), 0.59 (s, 6H), 1.01 (s, 18H), 6.92-6.98 (d, 4H, m), 8.36 (d, 2H, J=8.1 Hz)

$^{13}$C NMR (75 MHz, CDCl$_3$): δ −4.4, −1.6, 18.2, 25.8, 121.1, 123.7, 132.5, 134.6, 143.6, 158.6, 185.9

LRMS (ESI$^+$): m/z Found 145. calculated 145 for [M+H]$^+$.

(e) Synthesis of Compound Represented by the General Formula (I) (General Procedure)

A bromobenzene derivative (1.0 mmol) and anhydrous THF (5 mL) were put into a sufficiently dried flask inside of which was substituted with argon. The mixture was cooled to −78° C., and then added with 1 M sec-BuLi (0.5 mmol), and the mixture was stirred for 20 minutes. The mixture was slowly added with 3,6-diOTBDMS-X-xanthone (0.015 to 0.020 mmol) dissolved in anhydrous THF (5 mL) at the same temperature, and the mixture was returned to room temperature. The mixture was stirred at room temperature for 1 hour, and then added with 2 N HCl (10 mL), and the mixture was stirred for 20 minutes. The mixture was extracted with dichloromethane, and the organic layer was washed with brine. The organic layer was dried over Na$_2$SO$_4$, the solvent was removed, and then the residue was purified by HPLC to obtain a compound represented by the general formula (I).

(e) 2-Me Ge-TM

According to the method of (e) mentioned above, the objective substance was obtained (yield 99%)

$^1$H-NMR (300 MHz, D$_2$O): δ 0.42 (s, 6H), 1.80 (s, 3H), 6.11 (dd, 2H, J=2.2, 9.5 Hz), 6.79-6.86 (m, 5H), 7.06-7.26 (m, 4H)

HRMS (ESI$^+$): m/z Found 391.0755. calculated 391.0753 for [M+H]$^+$ (0.2 mmu).

Example 8

[Formula 23]

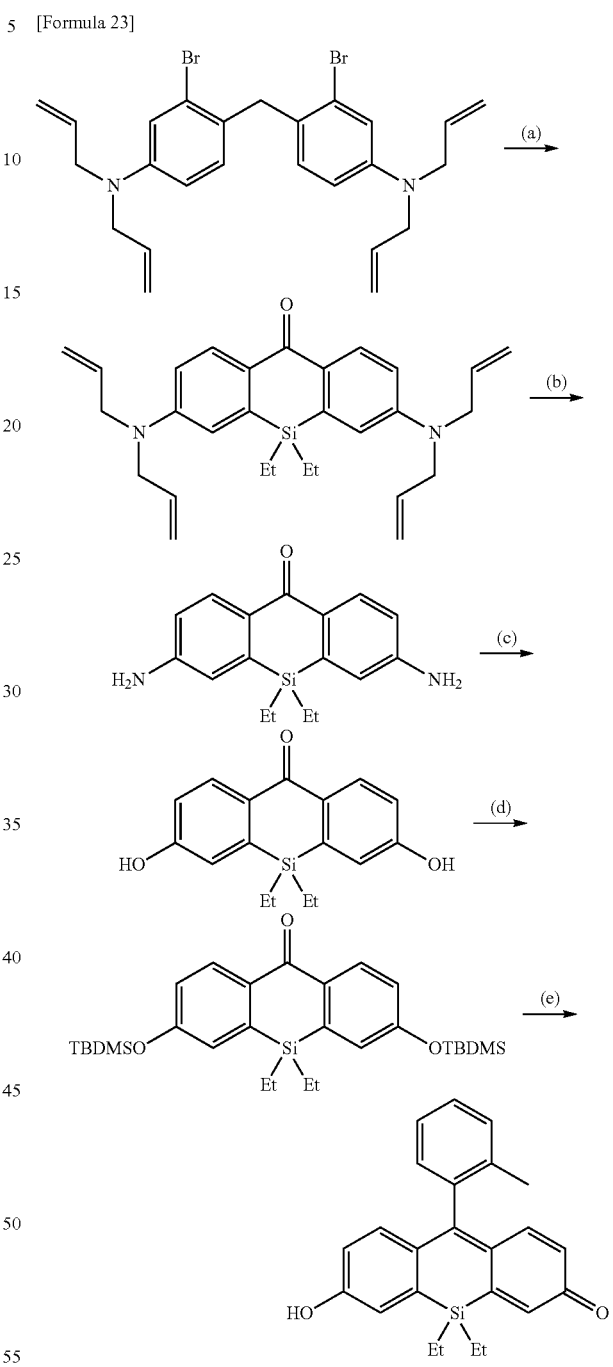

(a) N,N,N',N'-3,6-Tetraallyldiamino-diethyl-Si-xanthone

Bis(2-bromo-4-N,N-diallylaminophenyl)methane (1.65 g, 3.20 mmol) and anhydrous THF (20 mL) were put into a dried flask inside of which was substituted with argon. The mixture was cooled to −78° C., and then added with 1 M see-BuLi (10 mL, 10 mmol), and the mixture was stirred for 20 minutes. The mixture was slowly added with SiEt$_2$Cl$_2$ (1.04 mL, 7.02 mmol, Et represents ethyl group) dissolved in anhydrous THF (5 mL) at the same temperature, and the mixture was returned to room temperature, and stirred for 1 hour. The reaction was terminated with 2 N HCl, and the reaction mixture was neutralized with NaHCO$_3$. This mixture was extracted with dichloromethane, the organic layer was washed with brine, and dried over Na$_2$SO$_4$, and then the solvent was removed. The residue was dissolved in acetone (50 mL), and the solution was cooled to 0° C. This solution was added portionwise with KMnO$_4$ (1.49 g, 9.43 mmol) over 2 hours, and the mixture was further stirred at the same temperature for 1 hour. This mixture was added with dichloromethane (50 mL), and the mixture was filtered through Celite. Then, the solvent was removed, and the residue was purified by column chromatography (silica gel, hexane/ethyl acetate (10/1)) to obtain N,N,N',N'-3,6-tetraallyldiamino-diethyl-Si-xanthone (419 g, 0.917 mmol, yield 29%).

$^1$H NMR (300 MHz, CDCl$_3$): δ 0.91 (s, 10H), 4.01-4.02 (m, 8H) 5.17-5.22 (m, 8H), 5.82-5.94 (m, 4H), 6.79-6.84 (m, 4H), 8.35 (d, 2H, J=8.8 Hz)

$^{13}$C NMR (75 MHz, CDCl$_3$): δ 5.56, 7.48, 52.7, 113.3, 115.0, 116.5, 130.9, 131.6, 133.1, 138.3, 149.9, 185.3

HRMS (ESI$^+$): m/z Found 457.2661. calculated 467.2675 for [M+H]$^+$ (−1.5 mmu).

(b) 3,6-Diamino-diethyl-Si-xanthone

Pd(PPh$_3$)$_4$ (204 mg, 0.176 mmol) and 1,3-dimethylbarbituric acid (1.04 g, 6.67 mmol) were put into a dried flask inside of which was substituted with argon. The mixture was added with N,N,N',N'-tetraallyldiamino-diethyl-Si-xanthone (419 mg, 0.917 mmol) dissolved in dichloromethane (30 mL), and the mixture was stirred at 35° C. for 16 hours. The solvent was removed, the residue was suspended in saturated aqueous Na$_2$CO$_3$, and the suspension was extracted with dichloromethane. The organic layer was dried over Na$_2$SO$_4$, the solvent was removed, and then the residue was purified by column chromatography (silica gel, ethyl acetate/hexane (4/5)) to obtain 3,6-diamino-diethyl-Si-xanthone (236 mg, 0.796 mmol, yield 87%).

$^1$H NMR (300 MHz, CDCl$_3$): δ 0.83-0.95 (m, 10H), 4.10 (s, 4H), 6.76-6.81 (m, 4H), 8.33 (d, 2H, J=7.8 Hz)

$^{13}$C NMR (75 MHz, CDCl$_3$): δ 5.37, 7.38, 116.2, 117.5, 132.0, 132.9, 138.8, 148.9, 185.5

HRMS (ESI$^+$): m/z Found 297.1462. calculated 297.1423 for [M+H]$^+$ (3.9 mmu).

(c) 3,6-Dihydroxy-diethyl-Si-xanthone

The 3,6-Diamino-diethyl-Si-xanthone mixture (236 mg, 0.796 mmol) was dissolved in methanol/6 N H$_2$SO$_4$ (3/4, 35 mL). The solution was cooled to 0° C., and then slowly added with NaNO$_2$ (315 mg, 4.56 mmol) dissolved in H$_2$O (3 mL), and the mixture was stirred at the same temperature for 1 hour. The mixture was slowly added to boiling 1 N H$_2$SO$_4$ (50 mL), and the mixture was further refluxed for 10 minutes, and then cooled on ice. The reaction mixture was extracted with dichloromethane, and the organic layer was sufficiently washed with brine. The organic layer was dried over Na$_2$SO$_4$, the solvent was removed, and then the residue was purified by column chromatography (silica gel, ethyl acetate/hexane (1/1)) to obtain 3,6-dihydroxy-diethyl-Si-xanthone (74.3 mg, 0.249 mmol, yield 31%).

$^1$H NMR (300 MHz, CD$_3$OD): δ 0.83-1.04 (m, 10H), 6.99 (dd, 2H, J=2.2, 8.8 Hz), 7.09 (d, 2H, J=2.9 Hz), 8.31 (d, 2, J=8.8 Hz)

$^{13}$C NMR (75 MHz, CD$_3$OD): δ 6.07, 7.56, 118.4, 120.0, 133.4, 135.0, 140.9, 162.0, 187.9

HRMS (ESI$^+$): m/z Found 321.0964. calculated 321.0923 for [M+Na]$^+$ (4.1 mmu).

(d) 3,6-DiTBDMSO-diethyl-Si-xanthone

Dihydroxy-diethyl-Si-xanthone (74.3 mg, 0.249 mmol), and imidazole (326 mg, 4.79 mmol) were dissolved in dichloromethane (20 mL), the solution was slowly added with TBDMSCl (715 mg, 4.74 mmol) dissolved in dichloromethane (5 mL), and the mixture was stirred at room temperature for 14 hours. The mixture was added with H$_2$O, the mixture was extracted with dichloromethane, and the organic layer was washed with brine. The organic layer was dried over Na$_2$SO$_4$, the solvent was removed, and then the residue was purified by column chromatography (silica gel, ethyl acetate/hexane (1/30)) to obtain 3,6-diTBDMSO-diethyl-Si-xanthone (93.2 mg, 0.177 mmol, yield 71%).

$^1$H NMR (300 MHz, CDCl$_3$): δ 0.26 (s, 12H), 0.85-1.02 (m, 28H), 6.98-7.05 (m, 4H), 8.39 (d, 2H, J=8. Hz)

$^{13}$C NMR (75 MHz, CDCl$_3$): δ −4.14, 5.46, 7.45, 18.5, 25.8, 122.1, 123.9, 132.5, 135.8, 139.2, 158.7, 186.3

HRMS (ESI$^+$): m/z Found 527.2869. calculated 527.2833 for [M+H]$^+$ (3.6 mmu).

(e) 2-Me DiEtTM

According to the method of Example 8, the step (e), the objective substance was obtained (yield 94%).

$^1$H NMR (300 MHz, D$_2$O, CD$_3$OD): δ 0.78-1.00 (m, 10H), 1.94 (s, 3H), 8.26 (dd, 2H, J=2.6, 9.2 Hz) 6.88-6.98 (m, 5H), 7.24-7.39 (m, 3H)

HRMS (ESI$^+$): m/z Found 373.1621. calculated 373.1624 for [M+H]$^+$ (−0.3 mmu).

The optical characteristics of 2-Me TM, 2-Me Ge-TM, and 2-Me DiEtTM obtained in Example 1, 7, and 8, respectively, are shown in Table 2 mentioned below. In the table, the items attached with the letter a were measured in a phosphate buffer (pH 9), and the item attached with the letter b was measured in a 0.1 M phosphate buffer containing 1% DMSO.

TABLE 2

|  | $\lambda_{abs}{}^a$ (nm) | $\lambda_{fl}{}^a$ (nm) | $\Phi_{fl}{}^a$ | $pK_a{}^b$ |
| --- | --- | --- | --- | --- |
| 2-Me TM | 582 | 598 | 0.42 | 6.8 |
| 2-Me Ge-TM | 572 | 590 | 0.47 | 6.7 |
| 2-Me DiEtTM | 582 | 601 | 0.48 | 6.9 |

Example 9: Synthesis of 2-COOH TM

[Formula 24]

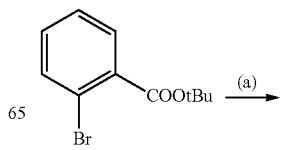

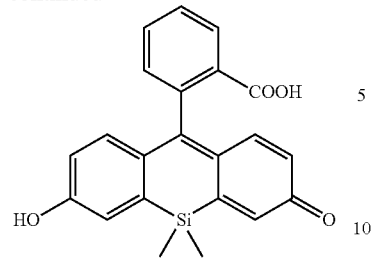

tert-Butyl 2-bromobenzoate (800 mg, 3.11 mmol) and anhydrous THF (5 mL) were put into a dried flask inside of which was substituted with argon. The mixture was cooled to −78° C., and then added with 1 M sec-BuLi (2.0 mmol), and the mixture was stirred for 20 minutes. The mixture was slowly added with 3,6-diOTBDMS-Si-xanthone (40.0 mg, 0.0802 mmol) dissolved in anhydrous THF (5 mL) at the same temperature, and the mixture was returned to room temperature. The mixture was stirred at room temperature for 30 minutes, and then added with 2 N HCl (10 mL), and the mixture was stirred for 20 minutes. The mixture was extracted with dichloromethane, and the organic layer was washed with brine, and dried over $Na_2SO_4$. The solvent was removed, then the residue was added with trifluoroacetic acid (TFA, 3 mL), and the mixture was stirred at room temperature for 1 hour. The solvent was removed, and then the residue was purified by HPLC to obtain 2-COOH TM (13.6 mg, 0.0358 mmol, yield 45%).

$^1$H-NMR (300 MHz, $CD_3COCD_3$): δ 0.56 (s, 3H), 0.64 (s, 3H), 6.76 (dd, 2H J=2.9, 8.8 Hz), 6.83 (d, 2H, J=8.8 Hz), 7.23 (d, 2H J=2.9 Hz), 7.38 (d, 1H, J=7.3 Hz), 7.67 (td, 1H, J=1.5, 7.3 Hz), 7.80 (td, 1H, J=1.5, 7.3 Hz), 7.94 (dd, 1H, J=1.5, 7.3 Hz)

$^{13}$C-NMR (100 MHz, $CD_3COCD_3$): δ −1.4, 0.2, 91.1, 117.6, 121.1, 125.5, 126.3, 127.0, 129.3, 130.1, 135.1, 136.7, 138.2, 155.3, 157.7, 170.4

HRMS (ESI$^+$): m/z Found 375.1018. calculated 375.1063 for [M+H]$^+$ (−3.5 mmu).

Example 10

[Formula 25]

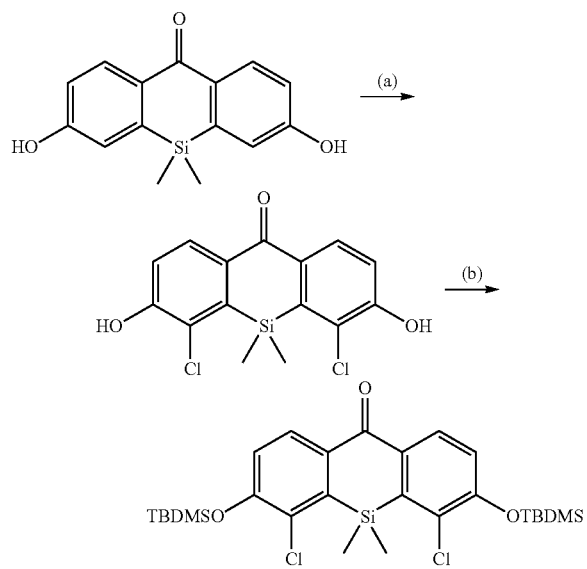

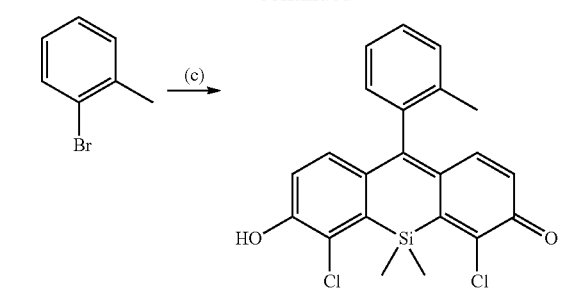

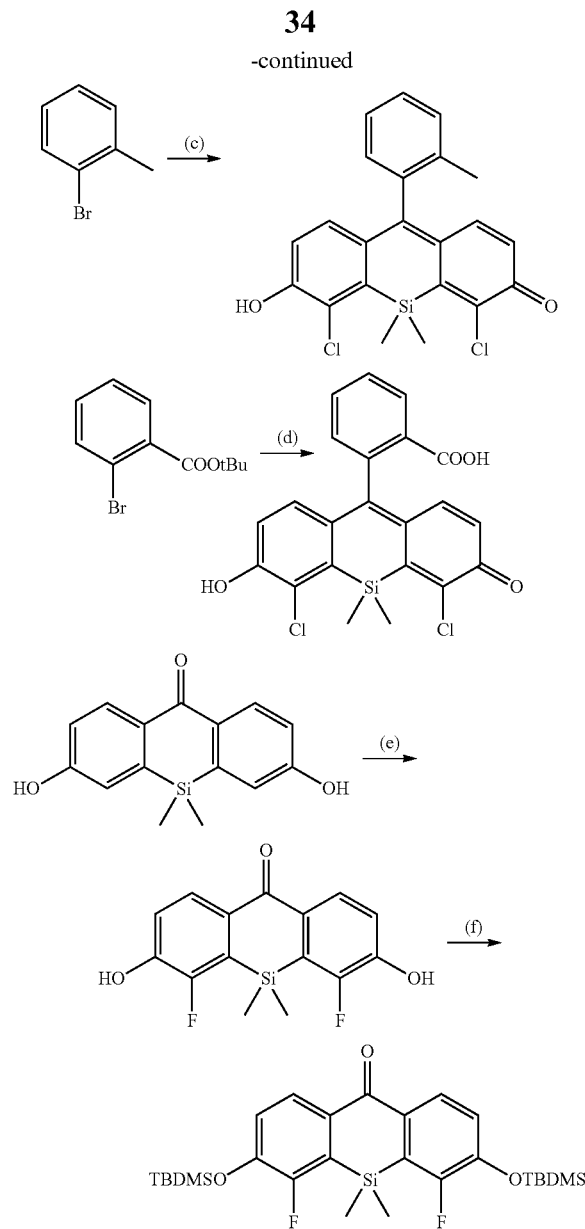

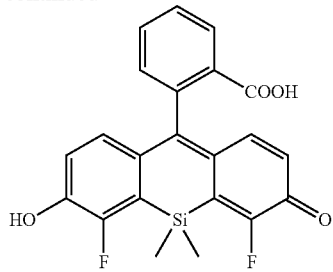

(a) 4,5-Dichloro-3,6-dihydroxy-Si-xanthone 3,6-Dihydroxy-Si-xanthone (81.1 mg, 0.300 mmol) was dissolved in methanol (5 mL), the solution was slowly added with 0.1 N NaOH (4 mL) in which NaOCl was dissolved at 100 mM, and the mixture was stirred at room temperature for 1 hour. The reaction mixture was adjusted to pH 2 by addition of 2 N HCl, and then extracted with ethyl acetate, and the organic layer was washed with brine. The organic layer was dried over $Na_2SO_4$, the solvent was removed, and then the residue was purified by column chromatography (silica gel, ethyl acetate/hexane (1/1)) to obtain 4,5-dichloro-3,6-dihydroxy-Si-xanthone (83.8 mg, 0.247 mmol, yield 82%).

$^1$H-NMR (400 MHz, $CD_3OD$): δ 0.80 (s, 1H), 7.11 (d, 2H, J=8.8 Hz), 8.27 (d, 2H, J=8.8 Hz)

$^{13}$C-NMR (100 MHz, $CD_3OD$): δ −1.6, 119.0, 127.0, 132.0, 133.8, 141.4, 158.4, 186.0

HRMS (ESI$^+$): m/z Found 339.0053. calculated 339.0011 for [M+H]$^+$ (4.2 mmu).

(b) 4,5-Dichloro-3,6-diOTBDMS-Si-xanthone 4,5-Dichloro-3,6-dihydroxy-Si-xanthone (69.0 mg, 0.203 mmol), and imidazole (54.5 mg, 0.801 mmol) were dissolved in dichloromethane (10 mL), the mixture was slowly added with TBDMSCl (121 mg, 0.803 mmol), and the mixture was stirred overnight at room temperature. The solvent was removed, and then the residue was purified by column chromatography (silica gel, dichloromethane) to obtain 4,5-dichloro-3,6-diOTBDMS-Si-xanthone (109 mg, 0.193 mmol, yield 95%).

$^1$H-NMR (400 MHz, $CDCl_3$): δ 0.30 (s, 12H), 0.81 (s, 6H), 1.06 (s, 18H), 7.06 (d, 2H, J=8.8 Hz), 8.35 (d, 2H, J=8.8 Hz)

$^{13}$C-NMR (100 MHz, $CDCl_3$): δ −4.3, −2.0, 18.4, 25.6, 121.5, 130.6, 131.0, 134.2, 140.5, 155.1, 184.9

HRMS (ESI$^+$): m/z Found 567.1731. calculated 567.1740 for [M+H]$^+$ (−0.9 mmu).

(c) 2-Me DCTM

2-Bromotoluene (17.1 mg, 0.100 mmol) and anhydrous THF (2 mL) were put into a dried flask inside of which was substituted with argon. The mixture was cooled to −78° C., and then added with 1 M sec-BuLi (0.10 mmol), and the mixture was stirred for 20 minutes. The mixture was slowly added with 4,5-dichloro-3,6-diOTBDMS-Si-xanthone (11.3 mg, 0.0200 mmol) dissolved in anhydrous THF (2 mL) at the same temperature, and the mixture was returned to room temperature. The mixture was stirred at room temperature for 1 hour, and then added with 2 N HCl (2 mL), and the mixture was stirred for 20 minutes. The mixture was extracted with dichloromethane, and the organic layer was washed with brine. The organic layer was dried over $Na_2SO_4$, the solvent was removed, and then the residue was purified by HPLC to obtain 2-Me DCTM (8.2 mg, 0.020 mmol, yield 99%).

$^1$H-NMR (300 MHz, $CD_3OD$): δ 0.87 (s, 3H), 0.87 (s, 3H), 2.04 (s, 3H), 6.57 (d, 2H, J=9.5 Hz), 6.90 (d, 2H, J=9.5 Hz), 7.10 (d, 2H, J=6.6 Hz), 7.32-7.47 (m, 3H)

HRMS (ESI$^+$): m/z Found 413.0526. calculated 413.0531 for [M+H]$^+$ (−0.6 mmu).

(d) 2-COOH DCTM tert-Butyl 2-bromobenzoate (129 mg, 0.502 mmol) and anhydrous THF (5 mL) were put into a dried flask inside of which was substituted with argon. The mixture was cooled to −78° C., and then added with 1 M sec-BuLi (0.30 mmol), and the mixture was stirred for 20 minutes. The mixture was slowly added with 4,5-dichloro-3,6-diOTBDMS-Si-xanthone (11.3 mg, 0.0200 mmol) dissolved in anhydrous THF (5 mL) at the same temperature, and the mixture was returned to room temperature. The mixture was stirred at room temperature for 1 hour, and then added with 2 N HCl (10 mL), and the mixture was stirred for 20 minutes. The mixture was extracted with dichloromethane, and the organic layer was washed with brine, and dried over $Na_2SO_4$. The solvent was removed, then the residue was added with TFA (5 mL), and the mixture was stirred at room temperature for 2 hours. The solvent was removed, and then the residue was purified by HPLC to obtain 2-COOH DCTM (5.7 mg, 0.013 mmol, yield 64%).

$^1$H-NMR (400 MHz, $CD_3OD$): δ 0.83 (s, 3H), 0.98 (s, 3H), 6.85 (d, 2H J=8.8 Hz), 6.89 (d, 2H, J=8.8 Hz), 6.98 (d, 1H J=7.8 Hz), 7.51 (td, 1H, J=1.0, 7.6 Hz), 7.60 (td, 1H, J=1.0, 7.6 Hz), 7.90 (d, 1H, J=7.8 Hz)

$^{13}$C-NMR (100 MHz, $CD_3COCD_3$): δ −0.2, 0.5, 90.0, 119.8, 123.6, 124.3, 126.4, 127.1, 127.8, 129.9, 135.1, 136.2, 136.7, 153.6, 158.3, 171.2

HRMS (ESI$^+$): m/z Found 443.0241. calculated 443.0273 for [M+H]$^+$ (−3.2 mmu).

(e) 4,5-Difluoro-3,6-dihydroxy-Si-xanthone 3,6-Dihydroxy-Si-xanthone (13.5 mg, 0.050 mmol) was dissolved in acetonitrile (3 mL), the solution was added with Selectfluor (registered trade mark, 35.4 mg, 0.1 mmol), and the mixture was refluxed overnight by heating at 80° C., and then purified by HPLC to obtain 4,5-difluoro-3,6-dihydroxy-Si-xanthone (4.1 mg, 0.013 mmol, yield 27%).

$^1$H-NMR (400 MHz, $CD_3OD$): δ 0.62-0.63 (m, 6H), 7.12 (m, 2H), 8.13 (d, 2H, J=8.8 Hz)

HRMS (ESI$^+$): m/z, Found 329.0393. calculated 329.0422 for [M+Na]$^+$ (−2.9 mmu).

(f) 4,5-Difluoro-3,6-diOTBDMS-Si-xanthone 4,5-Difluoro-3,6-dihydroxy-Si-xanthone (3.1 mg, 0.010 mmol) and imidazole (6.8 mg, 0.10 mmol) were dissolved in dichloromethane (2 mL), the solution was slowly added with TBDMSCl (15.1 mg, 0.10 mmol), and the mixture was stirred overnight at room temperature. The solvent was removed, and then the residue was purified by column chromatography (silica gel, dichloromethane) to obtain 4,5-difluoro-3,6-diOTBDMS-Si-xanthone (4.7 mg, 0.088 mmol, yield 88%).

$^1$H-NMR (400 MHz, CDCl$_3$): δ 0.25 (s, 12H), 0.64 (s, 6H), 1.02 (s, 18H), 7.09 (t, 2H, J=8.8 Hz), 8.20 (d, 2H, J=8.8 Hz)

HRMS (ESI$^+$): m/z Found 535.2380. calculated 535.2332 for [M+H]$^+$ (4.8 mmu).

(g) 2-Me DFTM

2-Bromotoluene (85.5 mg, 0.500 mmol) and anhydrous THF (3 mL) were put into a dried flask inside of which was substituted with argon. The mixture was cooled to −78° C., and then added with 1 M sec-BuLi (0.050 mmol), and the mixture was stirred for 20 minutes. The mixture was slowly added with 4,5-difluoro-3,6-diOTBDMS-Si-xanthone (5.4 mg, 0.010 mmol) dissolved in anhydrous THF (3 mL) at the same temperature, and the mixture was returned to room temperature. The mixture was stirred at room temperature for 1 hour, and then added with 2 N HCl (2 mL), and the mixture was stirred for 20 minutes. The mixture was extracted with dichloromethane, and the organic layer was washed with brine. The organic layer was dried over Na$_2$SO$_4$, the solvent was removed, and then the residue was purified by HPLC to obtain 2-Me DFTM (3.8 mg, 0.010 mmol, quant.).

$^1$H-NMR (300 MHz, D$_2$O): δ 0.60-0.64 (m, 6H), 1.94 (s, 3H), 6.42 (t, 2H, J=9.6 Hz), 6.90 (d, 2H, J=9.5 Hz), 6.95 (d, 1H, J=7.3 Hz), 7.22 (t, 2H, J=7.3 Hz), 7.32 (t, 1H, J=7.3 Hz), 7.44 (d, 1H, J=7.3 Hz)

HRMS (ESI$^+$): m/z Found 381.11145. calculated 381.1122 for [M+H]$^+$ (2.3 mmu).

(h) 2-COOH DFTM tert-Butyl 2-bromobenzoate (51 mg, 0.20 mmol) and anhydrous THF (3 mL) were put into a dried flask inside of which was substituted with argon. The mixture was cooled to −78° C., and then added with 1 M sec-BuLi (0.30 mmol), and the mixture was stirred for 20 minutes. The mixture was slowly added with 4,5-difluoro-3,6-diOTBDMS-Si-xanthone (5.4 mg, 0.010 mmol) dissolved in anhydrous THF (3 mL) at the same temperature, and the mixture was returned to room temperature. The mixture was stirred at room temperature for 1 hour, and then added with 2 N HCl (10 mL), and the mixture was stirred for 20 minutes. The mixture was extracted with dichloromethane, and the organic layer was washed with brine, and dried over Na$_2$SO$_4$. The solvent was removed, then the residue was added with TFA (3 mL), and the mixture was stirred at room temperature for 2 hours. The solvent was removed, and then the residue was purified by HPLC to obtain 2-COOH DFTM (2.2 mg, 0.054 mmol, yield 54%).

$^1$H-NMR (300 MHz, CD$_3$OD): δ 0.68 (s, 3H), 0.79 (s, 3H), 6.66 (d, 2H J=8.8 Hz), 6.87 (t, 2H, J=9.2 Hz), 7.13 (d, 1H J=7.3 Hz), 7.57-7.68 (m, 2H), 7.92 (d, 1H, J=8.1 Hz)

HRMS (ESI$^+$): m/z Found 411.0902. calculated 411.0864 for [M+H]$^+$ (3.8 mmu).

Example 11

[Formula 26]

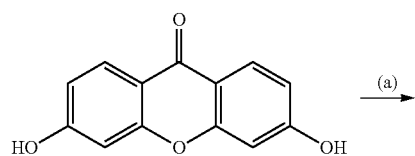

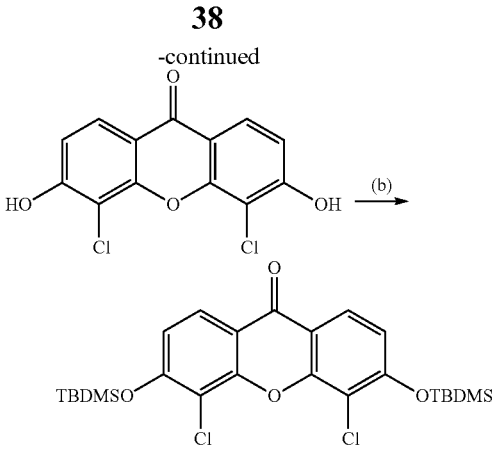

(a) 4,5-Dichloro 3,6-dihydroxyxanthone 3,6-Dihydroxyxanthone (45.6 mg, 0.200 mmol) was dissolved in methanol (5 mL), the solution was slowly added with 0.1 N NaOH (45 mL) in which NaOCl was dissolved at 10 mM, and the mixture was stirred overnight at room temperature. The reaction mixture was adjusted to pH 2 by addition of 2 N HCl, and then extracted with ethyl acetate, and the organic layer was washed with brine. The organic layer was dried over Na$_2$SO$_4$, the solvent was removed, and then the residue was purified by column chromatography (silica gel, ethyl acetate/hexane (2/1)) to obtain 4,5-dichloro-3,6-dihydroxyxanthone (57.3 mg, 0.193 mmol, yield 96%).

$^1$H-NMR (400 MHz, CD$_3$OD): δ 7.02 (d, 2H, J=8.8 Hz), 8.01 (d, 2H, J=8.8 Hz)

$^{13}$C-NMR (100 MHz, CD$_3$OD): δ 109.2, 114.7, 116.0, 126.4, 154.9, 161.2, 176.7

HRMS (ESI$^+$): m/z Found 318.9527. calculated 318.9541 for [M+Na]$^+$ (−1.4 mmu).

(b) 4,5-Dichloro-3,6-diOTBDMS-xanthone 4,5-Dichloro-3,6-dihydroxyxanthone (44.6 mg, 0.150 mmol) and imidazole (40.8 mg, 0.600 mmol) were dissolved in dichloromethane (10 mL), the solution was slowly added with TBDMSCl (90.4 mg, 0.600 mmol), and the mixture was stirred overnight at room temperature. The solvent was removed, and then the residue was purified by column chromatography (silica gel, dichloromethane) to obtain 4,5-dichloro-3,6-diOTBDMS-xanthone (68.2 mg, 0.130 mmol, yield 87%).

$^1$H-NMR (400 MHz, CDCl$_3$): δ 0.31 (s, 12H), 1.07 (s, 18H), 6.95 (d, 2H, J=8.8 Hz), 8.12 (d, 2H, J=8.8 Hz)

$^{13}$C-NMR (100 MHz, CDCl$_3$): δ −4.2, 18.4, 25.6, 113.8, 116.7, 117.1, 125.2, 153.5, 157.6, 175.2

HRMS (ESI$^+$): m/z Found 525.1495. calculated 525.1451 for [M+H]$^+$ (4.4 mmu).

The optical characteristics of 2-COOH TM, 2-Me DCTM, 2-COOH DCTM, 2-Me DFTM, and 2-COOH DFTM obtained in Examples 9 and 10 are shown in Table 3 mentioned below. The measurement was performed in a 0.1 M phosphate buffer (pH 9) containing 1% DMSO. pKa was obtained from the absorbance measured in a phosphate buffer (pH 9) by single-phase or two-phase curve fitting. The quantum yield was obtained by using the quantum yield of 2-Me TokyoMagenta (0.42) in a 0.1 M phosphate buffer (pH 9) as the standard.

TABLE 3

| Compound | $\lambda_{max, abs}$ (nm) pH 3 | pH 9 | $\lambda_{max, fl}$ (nm) | pKa | $\Phi_{fl}$ |
|---|---|---|---|---|---|
| 2-Me TM | 472 | 582 | 598 | 6.8 | 0.42 |
| 2-Me DCTM | 477 | 595 | 607 | 5.2 | 0.48 |
| 2-Me DFTM | 465 | 583 | 598 | 5.3 | 0.57 |
| 2-COOH TM | | 582 | 598 | 8.3, 7.6 | 0.38 |
| 2-COOH DCTM | | 591 | 607 | 7.1, 7.0 | 0.48 |
| 2-COOH DFTM | | 581 | 596 | 7.1, 6.9 | 0.54 |

Example 12

[Formula 27]

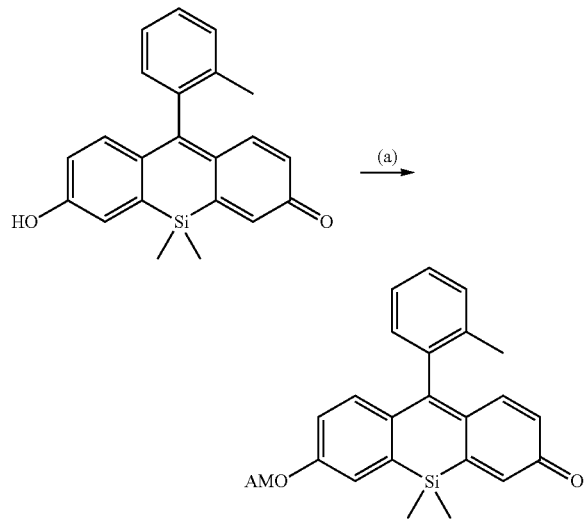

2-Me TM (10.6 mg, 0.0308 mmol) and diisopropylethylamine (DIEA, 17.4 μL, 0.0999 mmol) were dissolved in acetonitrile (5 mL), the solution was slowly added with acetic acid bromomethyl ester (9.8 μL, 0.10 mmol), and the mixture was stirred overnight at room temperature. The mixture was neutralized by addition of acetic acid, and then purified by HPLC to obtain 2-Me TMAM (8.9 mg, 0.021 mmol, yield 69%).

$^1$H-NMR (300 MHz, CDCl$_3$): δ 0.49 (s, 3H), 0.51 (s, 3H), 2.06 (s, 3H), 2.11 (s, 3H), 5.79 (s, 2H), 6.31 (dd, 1H, J=9.5, 2.2 Hz), 6.89-6.99 (m, 3H), 7.00 (dd, 1H, J=9.5, 2.2 Hz), 7.09 (d, 1H, J=8.1 Hz), 7.30-7.40 (m, 4H)

HRMS (ESI$^+$): m/z Found 417.1536. calculated 417.1522 for [M+H]$^+$ (1.4 mmu).

Example 13

[Formula 28]

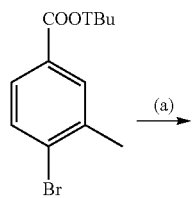

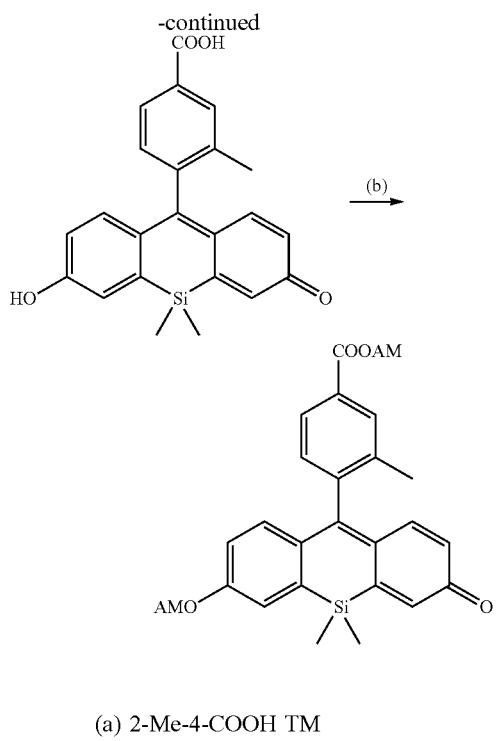

(a) 2-Me-4-COOH TM tert-Butyl 4-bromo-3-methylbenzoate (1.08 g, 3.98 mmol) and anhydrous THF (20 mL) were put into a dried flask inside of which was substituted with argon. The mixture was cooled to −78° C., and then added with 1 M sec-BuLi (4.0 mmol), and the mixture was stirred for 20 minutes. The mixture was slowly added with 3,6-diOTB-DMS-Si-xanthone (200 mg, 0.403 mmol) dissolved in anhydrous THF (10 mL) at the same temperature, and the mixture was returned to room temperature. The mixture was stirred at room temperature for 1 hour and then added with 2 N HCl (20 mL), and the mixture was stirred for 20 minutes. The mixture was extracted with dichloromethane, and the organic layer was washed with brine, and dried over Na$_2$SO$_4$. The solvent was removed, then the residue was added with TFA (20 mL), and the mixture was stirred at room temperature for 2 hours. The solvent was removed, and then the residue was purified by column chromatography (silica gel, methanol/dichloromethane (1/24)) to obtain 2-Me-4-COOH TM (148 mg, 0.381 mmol, yield 96%).

$^1$H-NMR (400 MHz, CD$_3$COCD$_3$): δ 0.51 (s, 3H), 0.53 (s, 3H), 2.14 (s, 3H), 6.50 (dd, 2H, J=2.4, 9.8 Hz), 6.84 (d, 2H, J=9.8 Hz), 7.11 (d, 2H, J=2.4 Hz), 7.31 (d, 1H, J=7.8 Hz), 8.03 (dd, 1H, J=1.0, 7.8 Hz), 8.05 (s, 1H)

$^{13}$C-NMR (100 MHz, CD$_3$COCD$_3$): δ −1.5, −1.3, 19.5, 123.0, 128.0, 130.1, 130.5, 131.4, 132.1, 137.5, 139.2, 145.0, 145.1, 146.3, 156.4, 167.4, 172.2

HRMS (ESI$^+$): m/z Found 389.1209. calculated 389.1209 for [M+H]$^+$ (0.0 mmu).

(b) 2-Me TMCOOAM

2-Me-4-COOH TM (1.9 mg, 0.0049 mmol) and DIEA (20 mg, 0.15 mmol) were dissolved in acetonitrile (1 mL), the solution was slowly added with acetic acid bromomethyl ester (25 mg, 0.16 mmol), and the mixture was stirred overnight at room temperature. The mixture was neutralized by addition of acetic acid, and then purified by HPLC to obtain 2-Me TMCOOAM (1.3 mg, 0.0024 mmol, yield 50%).

¹H-NMR (300 MHz, CD₃CN): δ 0.49-0.52 (m, 6H), 2.04 (s, 3H), 2.11 (s, 3H), 5.78 (s, 2H), 5.97 (s, 2H), 6.12 (dd, 1H, J=10.3, 2.2 Hz), 6.77 (d, 1H, J=8.8 Hz), 6.82 (d, 1H, J=2.2 Hz), 6.85 (d, 1H, J=10.3 Hz), 6.92 (dd, 1H, J=8.8, 2.9 Hz), 7.28 (d, 1H, J=8.1 Hz), 7.41 (d, 1H, J=2.9 Hz), 7.99 (d, 1H, J=8.1 Hz), 8.05 (s, 1H)

HRMS (ESI⁺): m/z Found 533.1596. calculated 533.1632 for [M+H]⁺ (−3.6 mmu).

Example 14

A compound in which a hydrophilic functional group was introduced into the benzene ring was synthesized as follows.

(a) 2-Me TMIDA

[Formula 29]

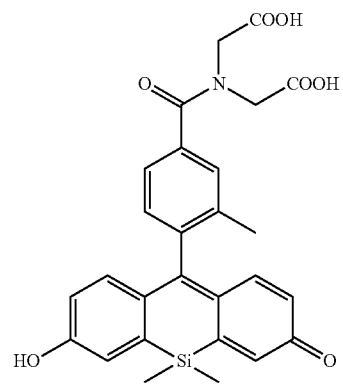

2-Me-4-COOH TM (77.6 mg, 0.200 mmol), HATU (114 mg, 0.300 mmol), HOBt-H₂O (46.9 mg, 0.300 mmol), di-tert-butyl iminodiacetate (490 mg, 2.00 mmol) and DIEA (258 mg, 2.00 mmol) were dissolved in DMF (20 mL), and the solution was stirred at room temperature for 3 hours. The solution was added with ethyl acetate (50 mL), and the organic layer was washed with 2 N HC, and then with brine. The organic layer was dried over Na₂SO₄, the solvent was removed, and then the residue was purified by column chromatography (silica gel, methanol/dichloromethane (1/24)). The resultant was added with trifluoroacetic acid (10 mL), and the mixture was stirred at room temperature for 1 hour. The solvent was removed, and then the residue was purified by HPLC to obtain 2-Me TMIDA (58.8 mg, 0.117 mmol, yield 59%).

¹H-NMR (300 MHz, CD₃COCD₃): δ 0.50 (s, 3H), 0.51 (s, 3H), 2.09 (s, 3H), 4.32 (s, 2H), 4.37 (s, 2H), 6.48 (dd, 2H, J=9.5, 2.2 Hz), 6.90 (d, 2H, J=9.5 Hz), 7.09 (d, 2H, J=2.2 Hz), 7.24 (d, 1H, J=7.3 Hz), 7.42 (dd, 1H, J=7.3, 1.5 Hz), 7.45 (d, 1H, J=1.5 Hz)

¹³C-NMR (75 MHz, CD₃COCD₃): δ −1.6, −1.3, 19.5, 48.5, 52.4, 123.0, 125.1, 129.5, 130.0, 130.3, 130.7, 136.4, 137.5, 139.4, 142.2, 145.2, 156.7, 170.7, 171.3, 172.1

HRMS (ESI⁺): m/z Found 504.1471. calculated 504.1479 for [M+H]⁺ (−0.8 mmu).

(b) 2-Me TMIDAAM

[Formula 30]

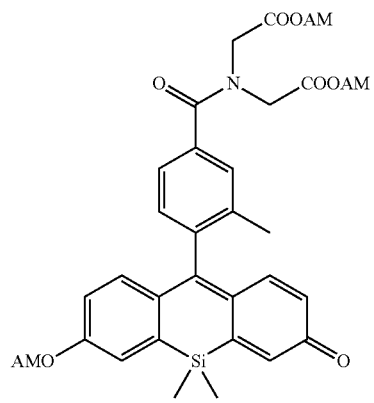

2-Me TMIDA (5.0 mg, 0.0099 mmol) and DIEA (3.5 μL, 0.020 mmol) were dissolved in acetonitrile (1 mL), the solution was slowly added with bromomethyl acetate (3.0 μL, 0.31 mmol), and the mixture was stirred overnight at room temperature. The mixture was slowly added with DIEA (3.5 μL, 0.020 mmol) and bromomethyl acetate (3.0 μL, 0.31 mmol), and the mixture was further stirred overnight at room temperature. The mixture was neutralized by addition of acetic acid, and then purified by HPLC to obtain 2-Me TMIDAAM (1.1 mg, 0.0015 mmol, yield 15%).

¹H-NMR (300 MHz, CD₃CN): δ 0.49-0.52 (m, 6H), 2.01 (s, 3H), 2.04 (s, 3H), 2.05 (s, 3H), 2.09 (s, 3H), 4.28-4.31 (m, 4H), 5.73 (s, 2H), 5.77 (s, 2H), 6.79 (s, 2H), 6.14 (d, 1H, J=10.3, 2.2 Hz), 6.81-6.98 (m, 4H), 7.19 (d, 1H, J=8.1 Hz), 7.33 (d, 1H, J=8.1 Hz), 7.38-7.43 (m, 2H)

HRMS (ESI⁺): m/z Found 720.2120. calculated 720.2112 for [M+H]⁺ (0.8 mmu).

(c) 2-Me TMIDAIDA

[Formula 31]

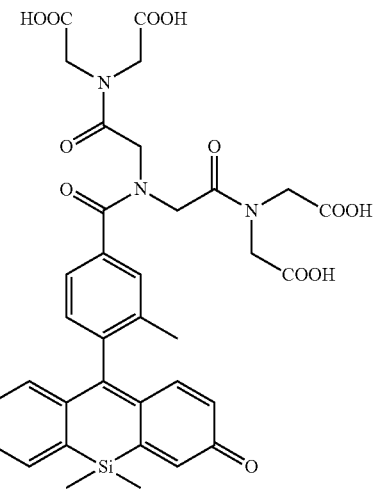

2-Me TMIDA (25.2 mg, 0.0500 mmol), HATU (190 mg, 0.500 mmol), HOBt-H₂O (77 mg, 0.50 mmol), di-tert-butyl iminodiacetate (245 mg, 1.00 mmol) and DIEA (129 mg, 1.00 mmol) were dissolved in DMF (5 mL), and the solution was stirred at room temperature for 8 hours. The solution was added with dichloromethane (60 mL), and the organic layer was washed with 2 N HCl, and then with brine. The organic layer was dried over $Na_2SO_4$, the solvent was removed, and then the residue was purified by column chromatography (silica gel, methanol/dichloromethane (1/24)). The resultant was added with trifluoroacetic acid (10 mL), and the mixture was stirred at room temperature for 2 hours. The solvent was removed, and then the residue was purified by HPLC to obtain 2-Me TMIDAIDA (5.2 mg, 0.0070 mmol, yield 14%).

$^1$H-NMR (300 MHz, $CD_3OD+NaOD$): δ 0.46 (s, 3H), 0.46 (s, 3), 2.10 (s, 3H), 3.80-4.00 (m, 8H), 4.49-4.55 (m, 4H), 6.29 (dd, 2H J=9.5, 2.9 Hz), 6.86 (d, 2H, J=9.5 Hz), 6.89 (d, 1H J=2.9 Hz), 7.19 (d, 1H, J=8.1 Hz), 7.54 (d, 1H, J=8.1 Hz), 7.58 (s, 1H)

HRMS (ESI$^+$): m/z Found 734.1985. calculated 734.2017 for $[M+H]^+$ (−3.2 mmu).

(d) 2-Me TMIDAIDAAM

[Formula 32]

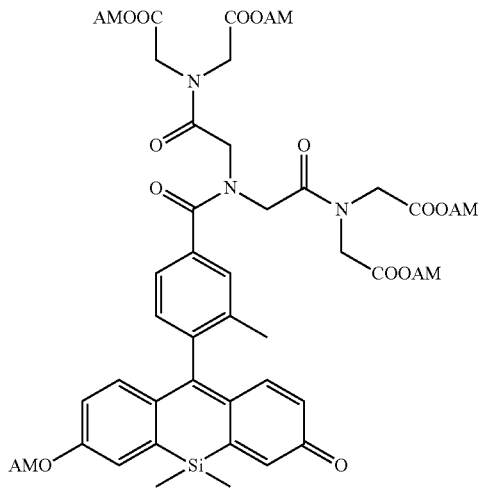

2-Me TMIDAIDA (2.7 mg, 0.0037 mmol) and DIEA (3.6 μL, 0.021 mmol) were dissolved in acetonitrile (3 mL), the solution was slowly added with bromomethyl acetate (2.0 μL, 0.020 mmol), and the mixture was stirred overnight at room temperature. The mixture was further added with DIEA (1.8 μL, 0.010 mmol) and bromomethyl acetate (1.0 μL, 0.010 mmol), and the mixture was stirred overnight at room temperature. The mixture was neutralized by addition of acetic acid, and then the tetra-AM eater compound as a reaction intermediate was purified by HPLC. The obtained intermediate (2.1 mg) and DIEA (3.6 μL, 0.020 mmol) were dissolved in acetonitrile (2 mL), the solution was slowly added with bromomethyl acetate (1.0 μL, 0.010 mmol), and the mixture was stirred at room temperature for two days. The mixture was neutralized by addition of acetic acid, and then purified by HPLC to obtain 2-Me TMIDAIDAAM (0.8 mg, 0.0007 mmol, yield 20%).

$^1$H-NMR (400 MHz, $CD_2Cl_2$): δ 0.38-0.43 (m, 6H), 1.96-2.04 (m, 18H), 3.98 (s, 2H), 4.12 (s, 2), 4.17 (s, 2H), 4.26 (s, 2), 4.29 (s, 2H), 4.34 (s, 2H), 5.59 (s, 2H), 5.64 (s, 2H), 5.67 (s, 2H), 5.69 (s, 2H), 5.73 (s, 2H), 6.09 (d, 1H, J=9.8 Hz), 6.72 (d, 1H, J=2.0 Hz) 6.82-6.90 (m, 3H), 7.09 (dd, 1H, J=7.8, 2.0 Hz), 7.22 (d, 1H, J=2.4 Hz), 7.30 (d, 1H, J=7.3 Hz), 7.36 (s, 1H)

HRMS (ESI$^+$): m/z Found 1094.3043. calculated 1094.3074 for $[M+H]^+$ (−3.1 mmu).

Example 15

Figure 13:
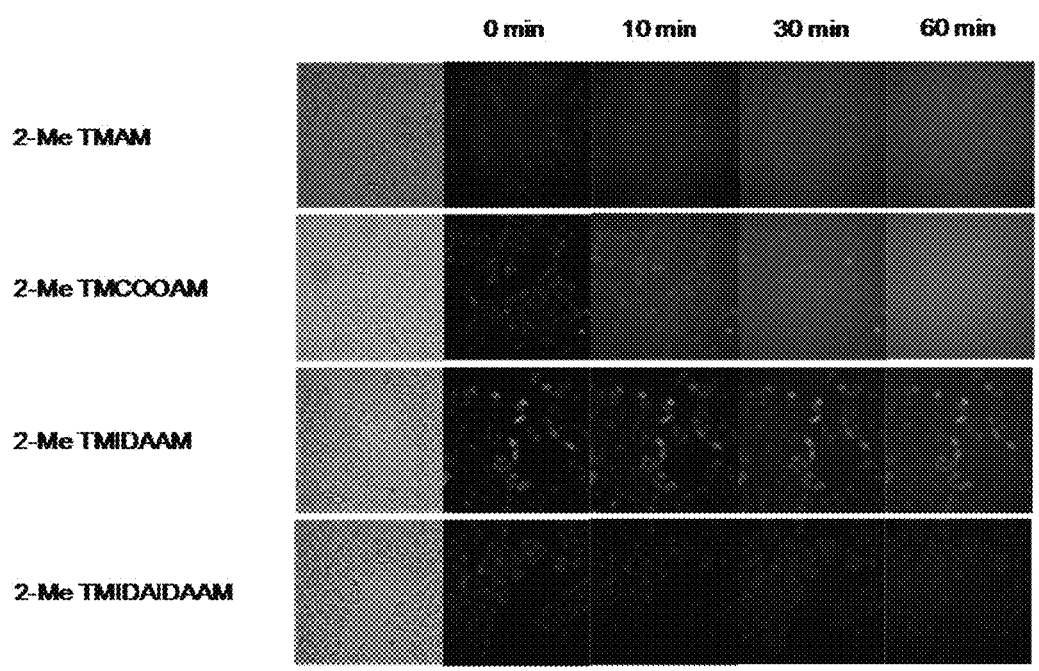
FIG. 13 shows results of measurement of fluorescence intensity change performed by loading 3 μM of each probe on HeLa cells at 37° C., washing off the probe, and then measuring fluorescence intensity under a microscope at 37° C. for 60 minutes. The probes were 2-Me TMAM (2000-4000), 2-Me TMCOOAM (1100-6000), 2-Me TMIDAAM (1000-5000), and 2-Me TMIDAIDAAM (550-800), exposure time was 30 ms, and ND means 6%.

Intracellular retentivity of the compounds introduced with a functional group having the hydrophilic IDA structure into the benzene ring was examined. It was demonstrated that the intracellular retentivity was improved by the introduction of the IDA structure, and thus imaging for a long period of time could be enabled (FIG. 13).

INDUSTRIAL APPLICABILITY

The compounds represented by the general formula (I) and salts thereof provided by the present invention show significantly deviated maximal absorption wavelengths of the non-dissociated form (neutral form) and dissociated form (anion form) compounds thereof and provide difference of the wavelengths about twice or more larger than the difference observed for fluorescein derivatives, and therefore they are useful as mother nucleus compounds for preparing a fluorescent probe enabling highly sensitive measurement of pH, reactive oxygen species, various enzymes, and the like without depending on the intramolecular photoinduced electron transfer and control of spiro ring cyclization.

What is claimed is:

1. A chemical compound represented by the following general having formula (IV):

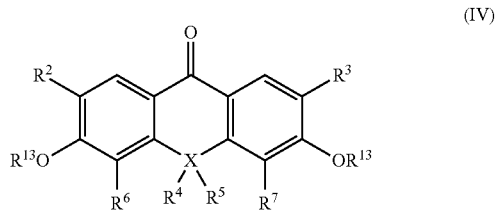

wherein, in the formula, $R^2$ and $R^3$ independently represent hydrogen atom, an alkyl group having 1 to 6 carbon atoms, or a halogen atom; $R^4$ and $R^5$ independently represent an alkyl group having 1 to 6 carbon atoms, or an aryl group having 1 to 6 carbon atoms; $R^6$ and $R^7$ independently represent hydrogen atom, an alkyl group having 1 to 6 carbon atoms, or a halogen atom; $R^{13}$ represents a protective group of phenolic hydroxy group; and X represents germanium atom, or tin atom, or a salt thereof.

2. The compound according to claim 1, wherein each of $R^6$ and $R^7$ represents a halogen atom.

3. The compound according to claim 2, wherein each of $R^2$ and $R^3$ represents a hydrogen atom.

4. The compound according to claim 1, wherein each of $R^2$, $R^3$, $R^6$ and $R^7$ represents a hydrogen atom.

5. A chemical compound having formula (IV):

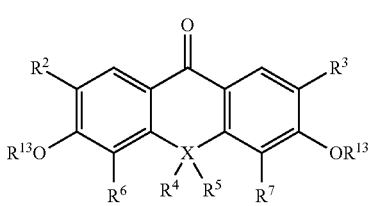

(IV)

wherein, in the formula, $R^2$ and $R^3$ independently represent hydrogen atom, an alkyl group having 1 to 6 carbon atoms, or a halogen atom; $R^4$ and $R^5$ independently represent an alkyl group having 1 to 6 carbon atoms, or an aryl group having 1 to 6 carbon atoms; $R^6$ and $R^7$ independently represent hydrogen atom, an alkyl group having 1 to 6 carbon atoms, or a halogen atom; $R^{13}$ represents a protective group of phenolic hydroxy group; wherein at least one of $R^2$, $R^3$, $R^6$ and $R^7$ represents an alkyl group having 1 to 6 carbon atoms, or a halogen atom; and X represents silicon atom, germanium atom, or tin atom, or a salt thereof.

6. The compound according to claim 5, wherein each of $R^6$ and $R^7$ represents a halogen atom.

7. The compound according to claim 6, wherein each of $R^2$ and $R^3$ represents a hydrogen atom.

8. A chemical compound having formula (IV):

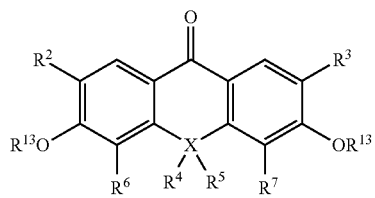

(IV)

wherein, in the formula, $R^2$ and $R^3$ independently represent hydrogen atom, an alkyl group having 1 to 6 carbon atoms, or a halogen atom; each of $R^4$ and $R^5$ represents an ethyl group; $R^6$ and $R^7$ independently represent hydrogen atom, an alkyl group having 1 to 6 carbon atoms, or a halogen atom; $R^{13}$ represents a protective group of phenolic hydroxy group; and X represents silicon atom, germanium atom, or tin atom, or a salt thereof.

9. The compound according to claim 8, wherein each of $R^6$ and $R^7$ represents a halogen atom.

10. The compound according to claim 9, wherein each of $R^2$ and $R^3$ represents a hydrogen atom.

11. The compound according to claim 8, wherein each of $R^2$, $R^3$, $R^6$ and $R^7$ represents a hydrogen atom.

* * * * *

UNITED STATES PATENT AND TRADEMARK OFFICE
CERTIFICATE OF CORRECTION

| | | |
|---|---|---|
| PATENT NO. | : 9,688,857 B2 | Page 1 of 1 |
| APPLICATION NO. | : 15/292858 | |
| DATED | : June 27, 2017 | |
| INVENTOR(S) | : T. Nagano et al. | |

It is certified that error appears in the above-identified patent and that said Letters Patent is hereby corrected as shown below:

In the Claims

Column 44, Lines 38, 39 (Claim 1, Lines 1, 2) please delete "represented by the following general"

Signed and Sealed this
Twelfth Day of December, 2017

Joseph Matal
*Performing the Functions and Duties of the
Under Secretary of Commerce for Intellectual Property and
Director of the United States Patent and Trademark Office*